(12) United States Patent
Alferiev et al.

(10) Patent No.: US 8,084,435 B2
(45) Date of Patent: Dec. 27, 2011

(54) BIODEGRADABLE LINKERS FOR MOLECULAR THERAPIES

(75) Inventors: Ivan Alferiev, Clementon, NJ (US); Robert J. Levy, Merion Station, PA (US); Ilia Fishbein, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 955 days.

(21) Appl. No.: 11/799,861

(22) Filed: May 3, 2007

(65) Prior Publication Data
US 2007/0298066 A1 Dec. 27, 2007

Related U.S. Application Data

(63) Continuation-in-part of application No. PCT/US2005/040106, filed on Nov. 4, 2005.

(60) Provisional application No. 60/625,386, filed on Nov. 5, 2004.

(51) Int. Cl.
| | |
|---|---|
| A61K 31/70 | (2006.01) |
| C12N 11/06 | (2006.01) |
| C12N 11/00 | (2006.01) |
| A01N 43/04 | (2006.01) |
| A61F 2/00 | (2006.01) |

(52) U.S. Cl. ....... 514/44; 435/174; 435/181; 424/78.08; 424/130.1; 424/423

(58) Field of Classification Search ................. 435/174, 435/181; 514/1.2, 6, 44, 12; 424/78.08, 424/94.1, 130, 194.1, 422, 486
See application file for complete search history.

(56) References Cited

U.S. PATENT DOCUMENTS

| | | | |
|---|---|---|---|
| 4,585,652 A | 4/1986 | Miller et al. | |
| 5,132,181 A * | 7/1992 | Wefers et al. | ................. 428/457 |
| 5,208,154 A | 5/1993 | Weaver et al. | |
| 5,648,506 A | 7/1997 | Desai | |
| 5,827,819 A | 10/1998 | Yatvin | |
| 6,143,037 A | 11/2000 | Goldstein et al. | |
| 6,273,913 B1 | 8/2001 | Wright et al. | |
| 6,333,194 B1 | 12/2001 | Levy et al. | |
| 6,639,014 B2 | 10/2003 | Pathak et al. | |
| 7,270,808 B2 * | 9/2007 | Cheng et al. | ............... 424/78.08 |
| 7,589,070 B2 * | 9/2009 | Levy et al. | .................. 514/44 R |
| 2003/0044408 A1* | 3/2003 | Levy et al. | ................. 424/130.1 |
| 2006/0147413 A1 | 7/2006 | Alferiev et al. | |

FOREIGN PATENT DOCUMENTS

| | | | |
|---|---|---|---|
| WO | WO 94/10149 | * | 5/1994 |
| WO | WO 95/00165 | * | 1/1995 |
| WO | WO 99/11703 | | 3/1999 |
| WO | WO 02/103004 | | 12/2002 |
| WO | WO 2004/022099 | | 3/2004 |
| WO | WO 2004/045578 | * | 6/2004 |
| WO | WO 2006/052790 | | 5/2006 |

OTHER PUBLICATIONS

Fishbein et al., Bisphosphonate-mediated gene vector delivery from the metal surfaces of stents PNAS Jan. 3, 2006 vol. 103 No. 1 159-164.*
Carter et al., Long-term effects of polymer-based, slow-release, sirolimus-eluting stents in a porcine coronary model Cardiovasc Res. Sep. 1, 2004;63(4):617-24. I.*
Fishbein et al. Local Delivery of Gene Vectors From Bare-Metal Stents by Use of a Biodegradable Synthetic Complex Inhibits In-Stent Restenosis in Rat Carotid Arteries; Circulation. 2008;117:2096-2103.).*
Saito et al., Drug delivery strategy utilizing conjugation via reversible disulfide linkages: role and site of cellular reducing activitiesAdvanced Drug Delivery Reviews vol. 55, Issue 2, Feb. 10, 2003, pp. 199-215.*
Engstler et al., ournal of Cell Science 117, 1105-1115 (2004) Kinetics of endocytosis and recycling of the GPI-anchored variant surface glycoprotein in Trypanosoma brucei.*
Life Science and analytical Products, 2003; Pierce, Rockford, IL pp. 104-105.*
Fishbein et al., Circulation 108 (suppl) 2003, p. IV-572.*
First Office Action from Chinese Patent Application No. 200580046037.7, with English Language Translation.
Extended European search report. Apr. 26, 2010 Birikaki, Lemonia.
U.S. Appl. No. 09/487,949, filed Jan. 19, 2000.
Feldman et al., "Optimal techniques for arterial gene transfer", Cardiovascular Research, 1997, pp. 391-404, vol. 35, France.
Roth et al., "Gene Therapy for Cancer: What Have We Done and Where Are We Going?", Journal of the National Cancer Institute, 1997, vol. 98, No. 1, pp. 21-39, Oxford University Press, England.
Smith et al., "Gene delivery systems for use in gene therapy: an overview of quality assurance and safety issues", Gene Therapy, 1996, pp. 190-200, vol. 3, Stockton Press, Scotland.
Tripathy et al., "Immune responses to transgene-encoded proteins limit the stability of gene expression after injection of replication-defective adenovirus vectors", Nature Medicine, 1996, pp. 545-550, vol. 2, No. 5, Nature Publishing Group, United States.
Nabel, "Gene Therapy for Cardiovascular Disease", Circulation, 1995, vol. 91, pp. 541-548, American Heart Association, United States.
Tzimagiorgis et al., "Introduction of the negative selection marker into replacement vectors by a single ligation step", Nucleic Acids Research, 1996, pp. 3476-3477, vol. 24, No. 17, Oxford University Press, England.

(Continued)

*Primary Examiner* — Maria Leavitt
(74) *Attorney, Agent, or Firm* — RatnerPrestia

(57) ABSTRACT

A method and a composition for delivery of a biomaterial to an animal cell or a tissue, the composition includes (a) a biomaterial; (b) a biodegradable cross-linker portion having a hydrolyzable bond, wherein the biodegradable cross-linker portion is covalently bound to the biomaterial; and (c) a substrate, wherein the substrate is covalently bound to the biodegradable cross-linker portion, provided that the biodegradable cross-linker is adapted to hydrolyze by breaking the hydrolyzable bond and thereby release and deliver the biomaterial. A process of making the composition is also provided.

1 Claim, 9 Drawing Sheets

OTHER PUBLICATIONS

Fasbender et al., "Complexes of Adenovirus with Polycationic Polymers and Cationic Lipids Increase the Efficiency of Gene Transfer in Vitro and in Vivo", 1997, pp. 3479-3489, vol. 272, No. 10, The Journal of Biological Chemistry, The American Society of Biochemistry and Molecular Biology, Inc., United States.

Lincoff et al., "Sustained Local Delivery of Dexamethasone by a Novel Intravascular Eluting Stent to Prevent Restenosis in the Porcine Coronary Injury Model", Journal of American College of Cardiology, 1997, pp. 808-816, vol. 29, No. 4, Elsevier Science, Inc., United States.

Bonadio et al., "Localized, direct plasmid gene delivery in vivo: prolonged therapy results in reproducible tissue regeneration", Nature Medicine, 1999, pp. 753-759, vol. 5, No. 7, Nature Publishing Group, United States.

Hermanson, "Bioconjugate Techniques", Pierce Chemical Company, 1996, pp. 56-70, Academic Press, San Diego, United States.

Chiu et al., "Synthesis of Temperature/pH-Sensitive Hydrogels Containing Disulfide Linkages as Cross-Links and Their Characterization", Polymer Journal, pp. 574-582, 2000, vol. 32, No. 7, Taiwan.

Appleby et al., "Gene Therapy for Restenosis-What Now, What Next?", Current Gene Therapy, 2004, pp. 153-182, vol. 4, Bentham Science Publishers, Ltd., Scotland.

Ropson et al., "Synthesis and Characterization of Biodegradable Homopolymers and Block Copolymers Based on Adipic Anhydride", Journal of Polymer Science, vol. 35 pp. 183-192, 1997, John Wiley & Sons, Inc., Belgium.

* cited by examiner

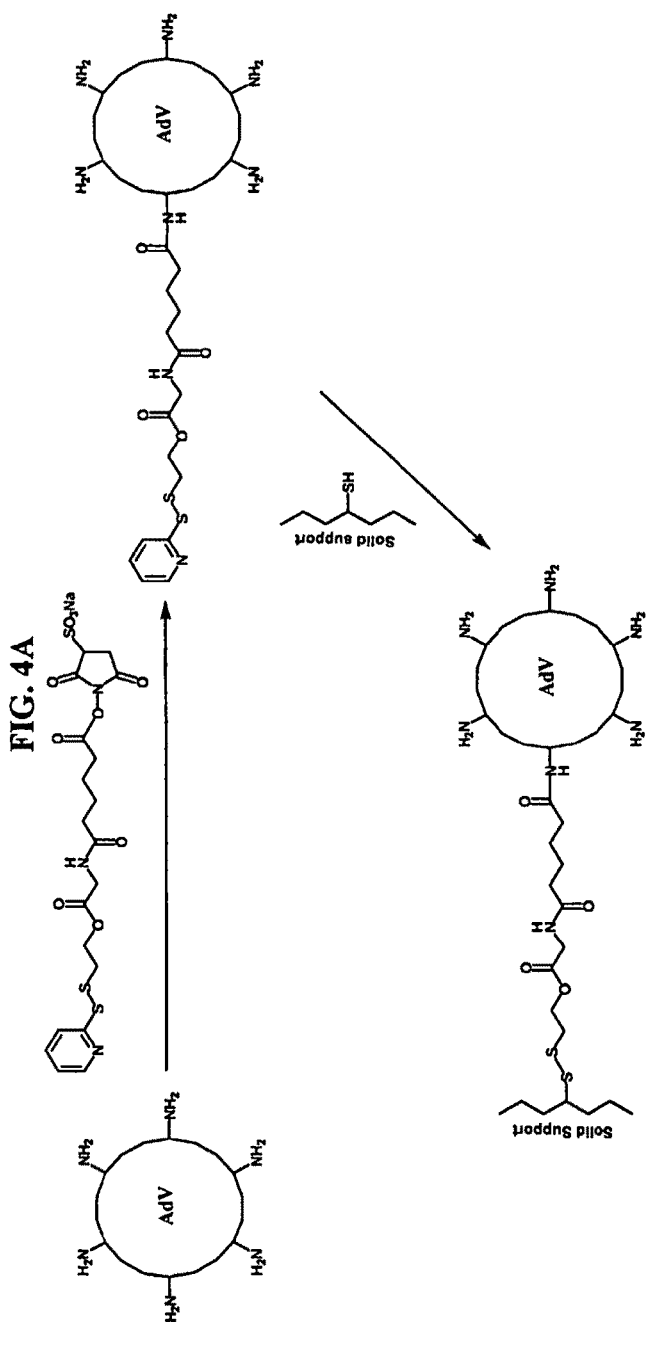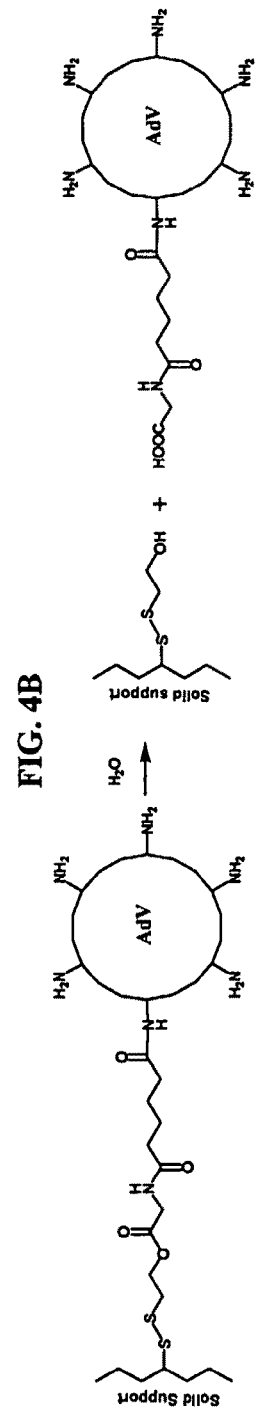
FIG. 4A
FIG. 4B

Figure 10. Significant reduction of in-stent restenosis in rat carotid studies with gene delivery stents using HL2 tethered AdiNOS compared to bare metal stents (controls). A)&B) depict control or iNOS-stented rat carotid arteries respectively, 100x; C) shows quantitation of inhibition of lumen obstruction, and D) the ratio of neointima to medial layers *in vivo*.

BIODEGRADABLE LINKERS FOR MOLECULAR THERAPIES

RELATED APPLICATIONS

This application is a continuation-in-part of PCT/US2005/040106, filed under 35 U.S.C. §365(c), and claims benefit to PCT/US2005/040106, filed Nov. 4, 2005, which claims priority to U.S. 60/625,386, filed Nov. 5, 2004. Both of these applications are incorporated herein by reference.

STATEMENT REGARDING FEDERALLY SPONSORED RESEARCH (IF APPLICABLE)

This research was supported in part by U.S. Government funds (National Heart Lung and Blood Institute grant number HL72108), and the U.S. Government may therefore have certain rights in the invention.

FIELD OF THE INVENTION

This invention relates to surface modifications and more particularly to cross-linking of molecules to surfaces and release of molecules upon biodegradation of cross-links.

BACKGROUND OF THE INVENTION

Delivery of various biomaterials including nucleic acids, proteins, cells, pharmaceutical agents and diagnostic agents has been a focus of intense research. Gene therapy is generally understood to refer to techniques designed to deliver nucleic acids, including antisense DNA and RNA, ribozymes, viral genome fragments and functionally active therapeutic genes into targeted cells (Culver, 1994, Gene Therapy: A Handbook for Physicians, Mary Ann Liebert, Inc., New York, N.Y.). Such nucleic acids can themselves be therapeutic, as for example antisense DNAs that inhibit mRNA translation, or they can encode, for example, therapeutic proteins that promote, inhibit, augment, or replace cellular functions. Success of gene therapy can be measured by ability to manipulate the rate and quality of gene delivery to an organism in need.

A serious shortcoming of current gene therapy strategies, including both ex vivo and in vivo gene therapy methods, is the inability of previously described vector and delivery system combinations to deliver nucleic acids efficiently into the interior of cells of a targeted population.

Virus vectors are generally regarded as the most efficient nucleic acid delivery vectors. Recombinant replication-defective virus vectors have been used to transduce (i.e., infect or transfect) animal cells both in vitro and in vivo. Such vectors include retrovirus, adenovirus, adeno-associated virus, and herpes virus vectors. Although they are highly efficient for gene transfer, one major disadvantage associated with the use of virus vectors is the inability of many virus vectors to infect non-dividing cells. Another serious problem associated with the use of virus gene vectors is the potential for such vectors to induce an immune response in a patient to whom they are administered. Such an immune response limits the effectiveness of the virus vector, since the patient's immune system rapidly clears the vector upon repeated or sustained administration of the vector. Furthermore, insertion of a gene into the genome of a cell by a virus vector can induce undesirable mutations in the cell. Other problems associated with virus gene vectors include inability to appropriately regulate gene expression over time in transfected cells, toxicity and other side effects caused by delivery of virus vectors to human tissues (e.g., liver damage and myocarditis), and potential production and transmission to other humans of harmful virus particles.

Furthermore, virus gene vectors, as used in prior art methods, frequently cannot be delivered to a selected tissue in a specific, localized manner. Instead, many prior art methods of administering virus vectors result in vector being dispersed systemically to tissues which adjoin, or are in fluid communication with, the desired target tissue. The inability of such methods to localize virus vectors reduces the utility of the methods, because a non-localized virus vector can transfect unintended tissues, elicit immune responses, be rapidly excreted from the body, or otherwise have a diminished transfection ability. A significant need exists for methods of delivering virus vectors in a localized manner.

Virus vectors can be used as vehicles to deliver proteins and other therapeutic molecules to the cells which the virus vectors transfect. Such proteins and other therapeutic molecules can be incorporated passively and non-specifically into virus vector particles. Alternatively, virus vectors specifically incorporate fusion proteins comprising a protein having a polypeptide viral packaging signal fused therewith.

Even though virus vectors have been widely used in experimental gene therapy protocols and human studies (Feldman et al., 1997, Cardiovasc. Res. 35:391-404; Roth et al., 1997, J. Natl. Cancer Inst. 89:21-39), none of these vectors has proven to be efficacious for a virus vector-mediated gene therapy. It has been hypothesized that the shortcomings of adenovirus vectors have been due, at least in part, to limited transgene expression resulting from the immune response of the host individual and cytotoxic effects toward organs of the host individual (Smith et al., 1996, Gene Ther. 3:190-200; Tripathy et al., 1996, Nat. Med. 2:545-549; Nabel et al., 1995, Gene Ther. Cardiovasc. Dis. 91:541-548). Other researchers have concentrated their efforts on mutating adenovirus vectors to render them relatively less immunogenic and toxic.

In addition to the low efficiency of a virus vector uptake exhibited by most cell types and low levels of expression of the gene constructs delivered by virus vectors, many targeted cell populations are found in such low numbers in the body that the efficiency of transfection of these specific cell types is even further diminished. Thus, there is a need for gene therapy methods which can be used to efficiently deliver virus vectors to targeted cell populations. Others working in the field have concentrated on attempting to specifically target adenovirus vectors to a particular cell type, for example, by attaching a specialized receptor ligand to the vectors (Tzimagiorgis et al., 1996, Nucl. Acids 24:3476-3477).

To be useful to gene delivery, a virus vector must be delivered to its target cells in a form in which the biochemical components of the virus vector retain their function. Specifically, the virus vector must retain the capacity to bind to target cells, to transfer a nucleic acid carried by the vector into the interior of the cell, and, in some circumstances, to catalyze chemical reactions involving that nucleic acid within the cell (e.g., reverse transcription, integration into the host cell genome, or promoting transcription of gene elements on the nucleic acid). Thus, it is important that the virus vector is administered to a patient without being exposed to chemically harsh or biochemically inactivating conditions. Further, many matrices are not compatible for contacting with virus vectors. Ideally, a matrix in or on which a virus vector is disposed should be biodegradable, and in a form suitable to use in surgical and therapeutic interventions.

Others have demonstrated enhancement of transfection effected by combining adenovirus vectors with polylysine or cationic lipids to form soluble virus vector complexes (Fasbender et al., 1997, J. Biol. Chem. 272:6479-6489). However, such virus complexes still exhibit many of the disadvantages described herein which are characteristic of virus vectors, including a short duration of the period during which the virus vector is available to contact with the desired tissue.

One approach to the biomaterial delivery is to coat a medical device with a composition comprising the biomaterial from which the biomaterial is released (e.g., U.S. Pat. No. 6,143,037 to Goldstein et al. and references therein). The problem with such coatings is that that they can invoke acute or chronic inflammatory responses due to the nature of coatings (see Lincoff et al., J. Am. Coll. Cardiol., 29, 808.16 (1997)). The nucleic acid delivery from coatings has also been problematic due to the limited ability to transfer a nucleic acid efficiently into a targeted cell population and achieve a high level of expression of the gene product in vivo. Further, current methods do not provide a sufficiently strong connection between the biomaterial and the delivery vehicle. For example, incorporating plasmid DNA into a collagen sponge and implanting it in bone can successfully deliver the nucleic acid but most of the DNA escapes in a very short time (e.g., less than one hour) (see Bonadio et al., Nat. Med. 1999, 5(7):753-9). Other known methods do not provide a sufficient release of biomaterial by ways other than biodegradation of the matrix, which may be too inefficient.

There have been attempts to solve these problems by incorporating biodegradable regions in a coating. See, for example, U.S. Pat. No. 6,639,014 to Pathak et al. disclosing a controlled release delivery of a biologically active material incorporated in biodegradable hydrogels. However, this approach does not solve the problem of insufficiently tight connection between the coating and the surface coated.

Inventors have demonstrated previously that gene therapy vectors can either be attached to surfaces or contained within other delivery systems using affinity adaptors (or connectors), such as specific antibodies or recombinant proteins (e.g., receptor fragments) (see U.S. patent application Ser. No. 09/487,949 by Levy et al., U.S. Patent Application Publication No. 2003/0044408A1 by Levy et al., and U.S. Pat. No. 6,333,194 to Levy et al.). Others have attempted to deliver charged bioactive agents to biological systems by reversibly binding charged bioactive agents to oppositely charged electrode surfaces, contacting the electrodes with the biological system, and thereafter relieving the charge on the electrode surface (e.g. U.S. Pat. Nos. 4,585,652 and 5,208,154). Such methods are severely limited by the necessity to have electrical leads connecting the electrodes to a power source and by the difficulty of effectuating the sustained release of the bioactive agent from the electrode surface. Thus, the usefulness of such compositions for a delivery of virus vectors to specific tissues is limited.

A critical need remains for compositions suitable to deliver biomaterial to desired tissues in a manner in which the period during which the biomaterial is administered is prolonged and immunogenicity associated with such administration is minimized. At the same time, such compositions should not adversely affect the biological activity of the biomaterial to be delivered (e.g., the transfecting efficiency of the vector). The compositions and methods of the invention described herein satisfy this need.

All references cited herein are incorporated herein by reference.

BRIEF SUMMARY OF THE INVENTION

The invention provides a method and a composition suitable for delivery of a biomaterial to an animal cell or tissue, the method comprising the steps of 1) providing a composition comprising (a) a biomaterial; (b) a biodegradable cross-linker portion having a hydrolyzable bond, wherein the biodegradable cross-linker portion is covalently bound to the biomaterial; and (c) a substrate, wherein the substrate is covalently bound to the biodegradable cross-linker portion, and wherein the biodegradable cross-linker portion is adapted to hydrolyze and to release the biomaterial by breaking the hydrolyzable bond; and (2) contacting the composition with the animal cell or the tissue for a period of time sufficient to allow the hydrolyzable bond to hydrolyze and release the biomaterial, wherein the biomaterial is delivered to the animal cell or tissue.

In certain embodiments, the biomaterial is a member selected from the group consisting of a nucleic acid, a gene vector, a protein, a peptide, and a cell. In certain embodiments, the biomaterial comprises a pharmaceutical agent.

In certain embodiments, the hydrolyzable bond comprises an acyl-oxygen bond.

In certain embodiments, the biodegradable cross-linker portion is a member selected from the group consisting of

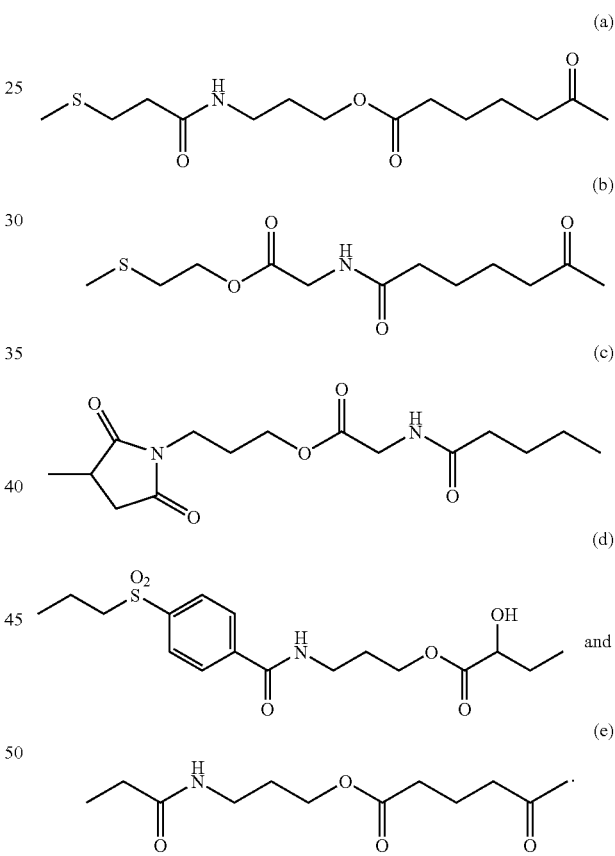

In certain embodiments, the substrate is a member selected from the group consisting of a metal, a metal oxide, a mineral, a ceramic, a polymer, a carbon, an organosylated material, and a metallo-organic material.

In certain embodiments, the biodegradable cross-linker portion is selected to affect a period of time sufficient to release and deliver the biomaterial.

In certain embodiments the substrate is a stent and the biomaterial comprises a compound that reduces in-stent restenosis.

Also provided is a process of making the composition of the invention, the process comprising: providing a biodegradable cross-linker having (a) the biodegradable cross-linker portion comprising the hydrolyzable bond, (b) a biomaterial-reactive end group, and (c) a substrate-reactive end group; providing a substrate having at least one reactive group; providing the biomaterial; reacting the substrate with the substrate-reactive end group of the biodegradable cross-linker to covalently attach the biodegradable cross-linker portion to the substrate; and reacting the biomaterial with the biomaterial reactive end group of the biodegradable cross-linker and thereby covalently attaching the biomaterial to the biodegradable cross-linker portion to make the composition.

In certain embodiments the composition is adapted to improve the stability of the biomaterial and protect a biomaterial from neutralization by antibodies In certain embodiments of the process, the substrate-reactive end group is a thiol-reactive group. In certain embodiments of the process, the biomaterial reactive end group is at least one of a sulfosuccinimidyl ester group, a tresylate group, and an epoxy group. In certain embodiments of the process, at least one reactive group of the substrate is a thiol group.

In certain embodiments of the process, the biodegradable cross-linker is a member selected from the group consisting of In certain embodiments of the process, the biomaterial is a member selected from the group consisting of a nucleic acid, a gene vector, a protein, a peptide, and a cell. In certain embodiments of the process, the biomaterial comprises a pharmaceutical agent.

In certain embodiments of the process, the substrate is a member selected from the group consisting of a metal, a metal oxide, a mineral, a ceramic, a polymer, a carbon, an organosylated material, and a metallo-organic material.

In certain embodiments of the process, the biomaterial is reacted with the biomaterial reactive end group prior to reacting the substrate with the substrate-reactive end group to form a biodegradable cross-linker modified biomaterial.

In certain embodiments of the process, providing the biodegradable cross-linker and reacting with the biomaterial comprise: providing (i) a first reactant having the biomaterial reactive end group and a first functional end group and (ii) a second reactant comprising (a) the biodegradable cross-linker portion comprising the hydrolyzable bond, (b) a second functional end group capable of reaction with the first functional end group, and (c) a substrate-reactive end group; reacting the biomaterial with the biomaterial reactive end group of the first reactant; and reacting the first functional group with the second functional group to form the biodegradable cross-linker modified biomaterial.

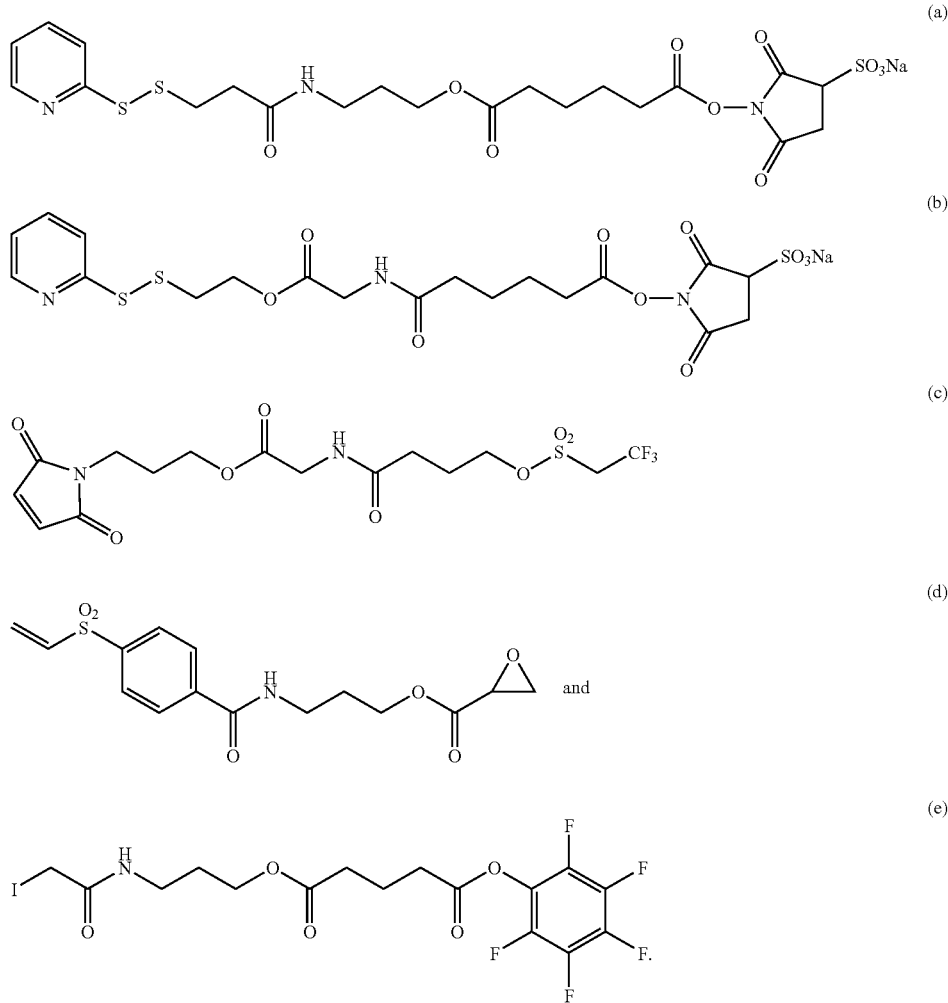

In one variant of this embodiment, the first reactant is maleimide-(sulfo)succinimidyl ester, male imide-tresylate or pyridyldithio-(sulfo)succinimidyl ester and the second reactant is dithiol, thiol-methyl sulfide or bis(methyl sulfide).

BRIEF DESCRIPTION OF THE DRAWINGS

The invention will be described in conjunction with the following drawings in which like reference numerals designate like elements and wherein;

FIG. 4A is a scheme depicting covalent immobilization of adenovirus (AdV or Ad) onto a solid support using the biodegradable linker 2.

FIG. 4B is a scheme depicting release of the immobilized adenovirus by cleavage of the bridge due to hydrolysis.

DETAILED DESCRIPTION OF THE INVENTION

The invention was driven by a desire to develop compositions and methods for covalently linking a biomaterial (e.g., gene vectors, recombinant proteins, cells, and pharmaceuticals) to a surface such that the biomaterial can be controllably released from the surface via a breakage of a bond in the selected biodegradable cross-linker upon exposure of the composition to hydrolysis. The invention can be used in a variety of applications for delivery of a biomaterial to a body or a cell. For example, covalent binding of a therapeutic viral vector to a coronary stent represents a new approach to antirestenotic gene therapy, as described in Example 10.

While investigating ways of attaching gene vectors to various surfaces, the inventors have observed that when commercially available bifunctional crosslinking agents, such as, for example, sulfosuccinimidyl 6-(3'-[2-pyridyldithio]-propionamido)hexanoate, are used to covalently bind a gene vector to a surface, the gene delivery was unsuccessful due to the failure of the vector to detach from the surface. This observation led the inventors to the present discovery, wherein a biodegradable hydrolysable bifunctional crosslinker is used to provide the desired covalent attachment of a gene vector to a surface and effectuate the retention of the vector function and hydrolysis of the linker with subsequent localized gene transfer.

Accordingly, the invention provides a composition for delivery of a biomaterial to an animal cell or a tissue, the composition comprising: (a) a biomaterial, (b) a biodegradable cross-linker portion having a hydrolyzable bond, wherein the biodegradable cross-linker portion is covalently bound to the biomaterial, and (c) a substrate, wherein the substrate is covalently bound to the biodegradable cross-linker portion, provided that the biodegradable cross-linker is adapted to hydrolyze by breaking the hydrolyzable bond and thereby release and deliver the biomaterial. In certain embodiments, the biomaterial is a nucleic acid, a gene vector, a protein, a peptide, or a cell. In certain embodiments, the biomaterial comprises a pharmaceutical agent.

The present invention is based upon the discovery that successful gene transfer to an arterial wall can be achieved by a covalent attachment of adenoviruses (Ad) to stents via a cleavable cross-linker, allowing for sustained release of functional Ad due to the cross-linker's hydrolysis. Exemplary amine-thiol-reactive bifunctional crosslinkers 1 (FIG. 1A) and 2 (FIG. 1B) incorporating a hydrolyzable ester bond were custom-synthesized. Model experiments demonstrated that $t_{1/2}$ of the ester bond hydrolysis in compound 1 was about several weeks at 37° C., whereas hydrolysis of compound 2 was an order of magnitude faster ($t_{1/2}$ nears several days under the same conditions). Thus, the inventors have discovered that by selecting the appropriate cross-linker, the time for release of biomaterial can be controlled.

Figure 5:
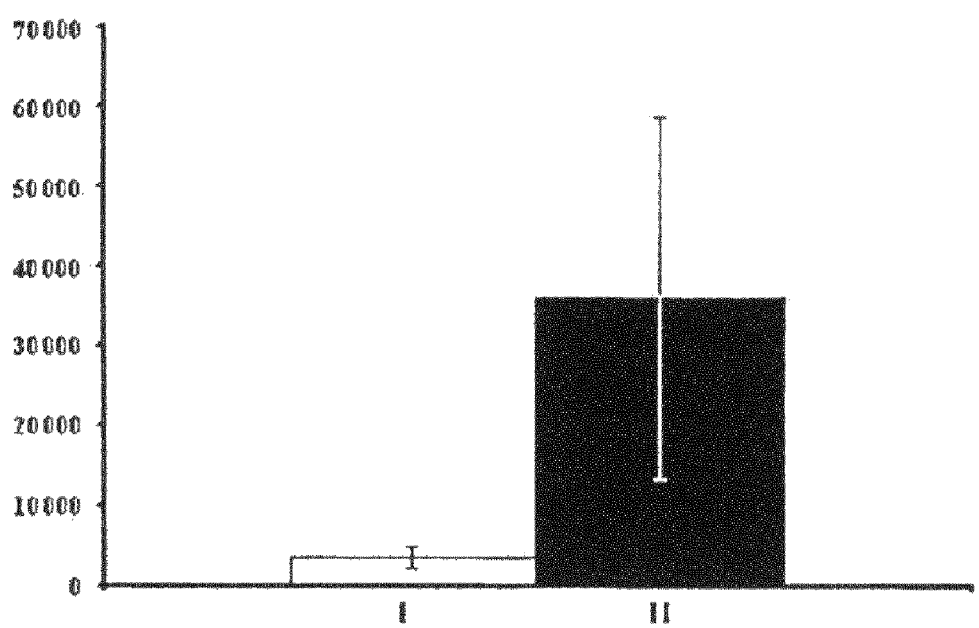
FIG. 5 is a bar graph depicting arbitrary fluorescence units, wherein the area I represents GFP transduction after 20 hours and the area II represents GFP transduction after 72 hours as described in the Example 4.

Recombinant adenoviral constructs Ad-GFP modified with hydrolyzable crosslinker 2 at a molar ratio 1:30 were coupled to stainless steel grids coated with a monolayer of thiolated polyallylamine bisphosphonate. Attainment of a physically robust, rubbing (abrasion)-resistant Ad layer on an activated stainless steel surface was visualized using a virus vector labeled with a fluorescent dye, Cy3. In the SMC culture (A10 cells), stainless steel grids with covalently bound Ad-GFP provided strictly localized transgene expression that increased 10-fold between 20 and 72 hours following transduction initiation reflecting exponential release of Ad due to the cross-linker's hydrolysis (FIG. 5). Stainless steel stents similarly modified with covalently attached Ad-GFP resulted in a massive medial and adventitial transduction 4 days after deployment in the rat carotid model (n=6) as demonstrated by fluorescent microscopy and immunohistochemistry. These results confirmed successful delivery of a biomaterial in vitro and in vivo via a composition of the invention.

In certain embodiments the biomaterial is tethered to a substrate with a biodegradable, hydrolysable, bifunctional crosslinker to improve the stability of the biomaterial at high and low temperatures, (below 10° C. and above 30° C., e.g., 37° C.—mammalian body temperature), and/or during storage.

In certain embodiments the biomaterial is tethered to a substrate with a biodegradable, hydrolysable, bifunctional crosslinker to prevent neutralization of the biomaterial by antibodies. The effects of antibody neutralization include inactivation of proteins and peptides, inhibition of viral infection, inhibition of receptor binding, and activation of the complement system which leads to degradation of the biomaterial.

media; $F_t$ is a substrate-reactive end group, preferably a thiol-reactive group (pyridyldithio, maleimide, vinyl sulfone, iodoacetamide, etc.).

In certain embodiments, the hydrolyzable bond comprises an acyl-oxygen bond. Non-limiting examples of the biodegradable cross-linker of the invention are shown in FIGS. 1A-E and have the following formulas (a)-(e):

(a)

(b)

(c)

(d)

and (e)

Components of the composition of the invention will now be described in detail.

Biodegradable Cross-Linker

A biodegradable cross-linker of the invention comprises (a) a biodegradable cross-linker portion comprising a hydrolyzable bond, (b) a biomaterial-reactive end group, and (c) a substrate-reactive end group. The biodegradable cross-linker can be described using the following general formula:

$F_t\text{-}A^1\text{-}D\text{-}A^2\text{-}F_p$ where $F_p$ is a biomaterial-reactive end group which enables covalent binding the rest of linker ($F_t$-$A^1$-D-$A^2$-) to the residues of amino-acids (lysine, methionine, etc.); $A^1$ and $A^2$ are aliphatic or aromatic bridges or moieties, which also may contain heteroatoms (e.g., O, S, NH, etc.); D is a bridge or a moiety degradable under physiological conditions and comprising an ester of carboxylic or carbamoic acids, or other bridge capable of gradual non-enzymatic cleavage in aqueous Preferred cross-linkers are cross-linkers of formulas (a) and (b), and most preferred is a cross-linker of formula (b).

In certain embodiments, the substrate-reactive end group is a thiol-reactive group. In certain embodiments, the biomaterial reactive end group is at least one of a sulfosuccinimidyl ester group, a tresylate group, and an epoxy group. The choice of the substrate-reactive end group and the biomaterial reactive end group will depend upon the choice of reactive groups on the selected surface and the biomaterial. For example, if the reactive group of the surface is a thiol group, the substrate-reactive end group is a thiol-reactive group such as, for example, pyridyldithio, maleimido, vinylsulfonyl, epoxy or iodoacetamido groups. Similarly, if the biomaterial has a reactive group, which is an amino group, the biomaterial reactive end group will be the group capable of reacting with amino groups such as, for example, a sulfosuccinimidyl ester group, a tresylate group, an epoxy group, a pentafluorophenyl ester group, etc. It is possible that both the substrate-reactive end group and the biomaterial reactive end group are the same or are capable of reacting with the same groups, however, different groups are preferred, and care should be taken to select groups such that the substrate-reactive end group and the biomaterial reactive end group do not react with each other as to preclude reacting with a surface and/or a biomaterial. Those skilled in the art will know how select appropriate groups without undue experimentation.

Figure 1A:
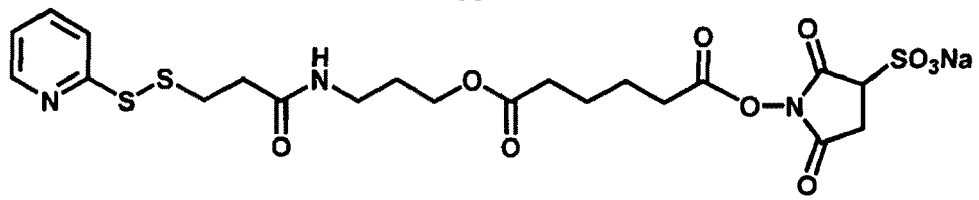
FIG. 1A is a scheme depicting a biodegradable cross-linker 1 having a protein-reactive sulfosuccinimidyl ester group and a surface-reactive pyridyldithio group.
Figure 1B:
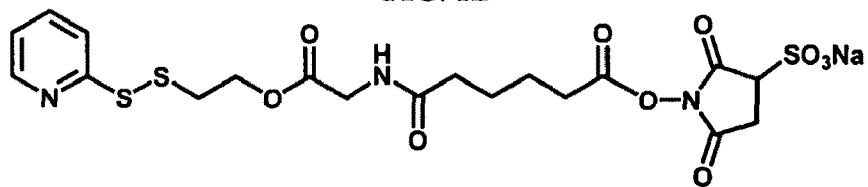
FIG. 1B is a scheme depicting a biodegradable cross-linker 2.
Figure 1C:
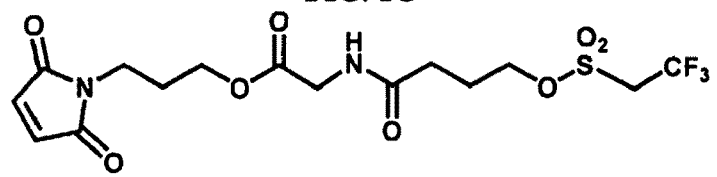
FIG. 1C is a scheme depicting a biodegradable linker with a tresylate (protein-reactive) group and a maleimide (thiol-reactive) group.
Figure 1D:
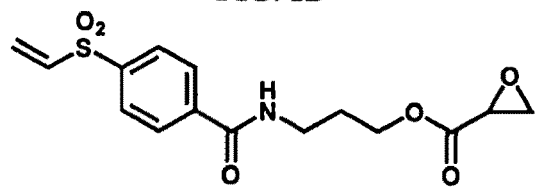
FIG. 1D is a scheme depicting a biodegradable linker with an epoxy (protein-reactive) group and a vinylsulfone (thiol-reactive) group.
Figure 1E:
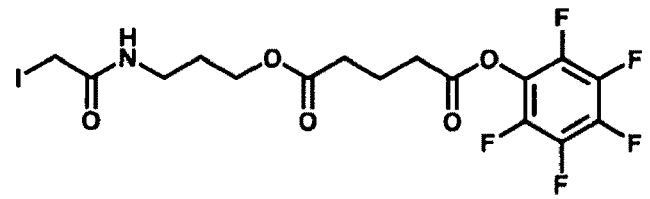
FIG. 1E is a scheme depicting a biodegradable linker with a pentafluorophenyl ester (protein-reactive) group and iodoacetamido (thiol-reactive) group.

Two biodegradable hetero-bifunctional (amino- and thiol-reactive) cross-linkers 1 and 2 with hydrolytically cleavable spacers (FIGS. 1A and 1B, formulas (a) and (b) respectively) were synthesized as described below.

Figure 2:
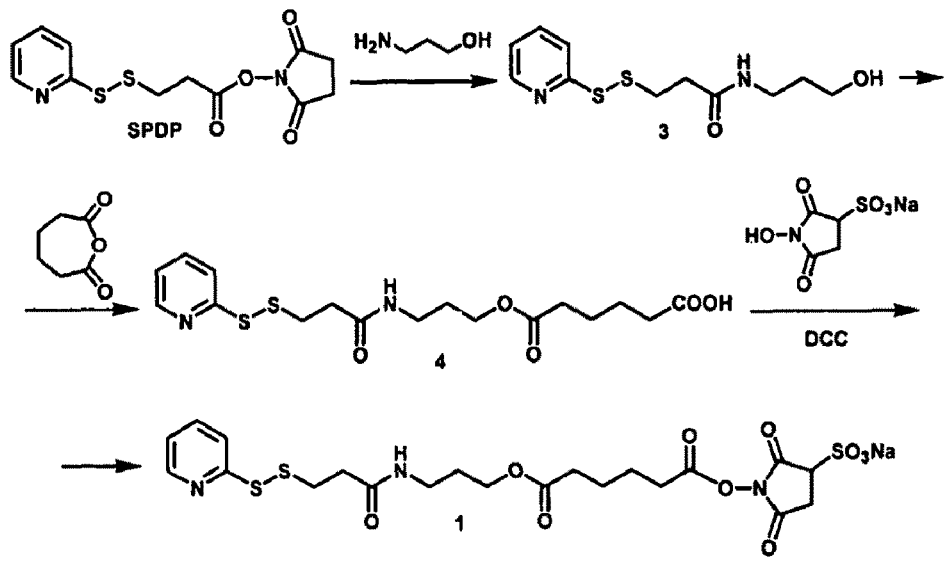
FIG. 2 is a scheme depicting the synthesis of the biodegradable cross-linker 1.

To prepare the cross-linker 1, SPDP was reacted with 3-aminopropanol, and the resulting alcohol 3 was acylated with adipic anydride, forming the acid 4 containing an ester bond. Finally, the cross-linker 1 was prepared via esterification of compound 4 with N-hydroxysulfosuccinimide and dicyclohexylcarbodiimide (DCC) (FIG. 2).

Pyridyldithio-Alcohol 3.

3-Aminopropanol (0.76 ml, 10 mmol) was dissolved in a mixture of $CH_2Cl_2$ (5 ml) and 2-propanol (3 ml) and cooled in an ice bath. A solution of SPDP (1.23 g, 3.9 mmol) in $CH_2Cl_2$ (2 ml) was added dropwise in ca. 1 min. The mixture was stirred in the cooling bath for 1.25 h, and a 13% aqueous solution of $NaH_2PO4$ (15 ml) and 85% $H_3PO_4$ (0.5 ml) were added. The products were extracted with ethyl acetate (2×30 ml), the organic layers were washed with 13% $NaH_2PO_4$, 15% $KHCO_3$ and dried in vacuo. The crude compound 3 (1.14 g) was purified by flash-chromatography on silica-gel, elution with mixtures of $CHCl_3$ and 2-propanol (100:0 to 100:7 by volume). Yield of pure compound 3 was 1.01 g (94%). TLC of compound 3 ($CHCl_3$-2-propanol, 9:1): one spot, $R_f$ ca. 0.3. $^1H$ NMR of compound 3 ($CDCl_3$), δ, ppm: 1.68 (quint., 6 Hz, 2H), 2.60 (t, 7 Hz, 2H), 3.05 (t, 7 Hz, 2H), 3.4 (br., 1H), 3.42 (q, 6 Hz, 2H), 3.62 (br., 2H), 6.99 (br., 1H), 7.10 (m, 1H), 7.58-7.65 (m, 1H).

Pyridyldithio-Carboxylic Acid 4.

The alcohol 3 (1.44 g, 5.3 mmol) was dissolved in $CH_2Cl_2$ (6 ml), and adipic anhydride (1.74 g, 13.6 mmol) was added (for preparation see: N. Ropson, P. H. Dubois, R. Jerome and P. H. Teyssie: Synthesis and characterization of biodegradable homopolymers and block copolymers based on adipic anhydride. Journal of PolymerScience: PartA: Polymer Chemistry 1997, 35, 183-192). The mixture was dried in vacuo to a syrup (3.29 g), allowed to react at 22° C. for 8 h and diluted with pyridine (5 ml). After stirring for 10 min., water (55 ml) was added, and the mixture was vacuum-concentrated at 35-40° C. to ca. 30 g. The acid 4 was extracted with $CHCl_3$ (2×50 ml) and re-extracted into 4% $KHCO_3$ ((3×40 ml). The aqueous phase was acidified with $H_3PO4$ to pH=3, the acid 4 was extracted with $CHCl_3$ (3×40 ml), and the crude compound (2.59 g) was purified by flash-chromatography on silica-gel, elution with mixtures of $CHCl_3$ and 2-propanol (100:0 to 100:8 by volume). Yield of pure compound 4 was 1.78 g (84%). TLC of compound 4 ($CHCl_3$-2-propanol, 9:1): one spot, $R_f$ ca. 0.5. $^1H$ NMR of 4 ($CDCl_3$), δ, ppm: 1.70 (m, 4H), 1.88 (quint., 6 Hz, 2H), 2.36 (t, 7 Hz, 2H), 2.38 (t, 7 Hz, 2H), 2.61 (t, 7 Hz, 2H), 3.05 (t, 7 Hz, 2H), 3.36 (q, 6 Hz, 2H), 4.15 (t, 6 Hz, 2H), 6.96 (br. t, 1H), 7.16 (m, 114), 7.66-7.73 (m, 2H), 8.44 (m, 1H).

Biodegradable Hetero-Bifunctional Cross-Linker 1.

The acid 4 (0.934 g, 2.33 mmol) was dissolved in N,N-dimethylacetamide (17 ml). Disodium salt of N-hydroxysulfosuccinimide (Pierce, 0.469 g, 2.16 mmol), dicyclohexylcarbodiimide (1.00 g, 4.85 mmol) and water (2.0 ml) were added consequently, and the mixture was stirred at 20-22° C. for 4 h. The precipitate of dicyclohexylurea was filtered off, the filtrate was vacuum-concentrated (at up to 0.1 mm Hg and no more than 30° C.) to a syrup (2.5 g). The syrup was thoroughly washed with hexane in several portions (totally, 140 ml) and triturated with ethyl acetate (45 ml) until solidification. After overnight standing at 4° C., the solid was filtered off, washed with tert-butanol (30 ml), ethyl acetate (60 ml) and dried in vacuo. The crude 1 (1.215 g) was purified by dissolution in methanol (30 ml) dilution with ethanol (30 ml), filtration through a layer of Cellulose CC 31 (Whatman) and vacuum-concentration of the filtrate to a suspension (6.9 g), with the following filtration, washing with ethanol and drying in vacuo. Yield of the pure cross-linker 1 was 1.06 g (80%). $^1H$ NMR of 1 (DMSO-$d_6$), δ, ppm: 1.62 (m, 4H), 1.69 (quint., 7 Hz, 2H), 2.33 (t, 7 Hz, 2H), 2.49 (t, 7 Hz, 2H), 2.68 (t, 7 Hz, 2H), 2.85 (dd, 18, 2 Hz, 1H), 3.01 (t, 7 Hz, 2H), 3.10 (q, 7 Hz, 2H), 3.16 (br., 1H), 3.94 (br. d, 1H) 4.01 (t, 7 Hz, 2H), 7.25 (m, 1H), 7.76 (m, 1H), 7.83 (m, 1H), 8.00 (br. t, 6 Hz, 1H), 8.46 (m, 1H).

Figure 3:
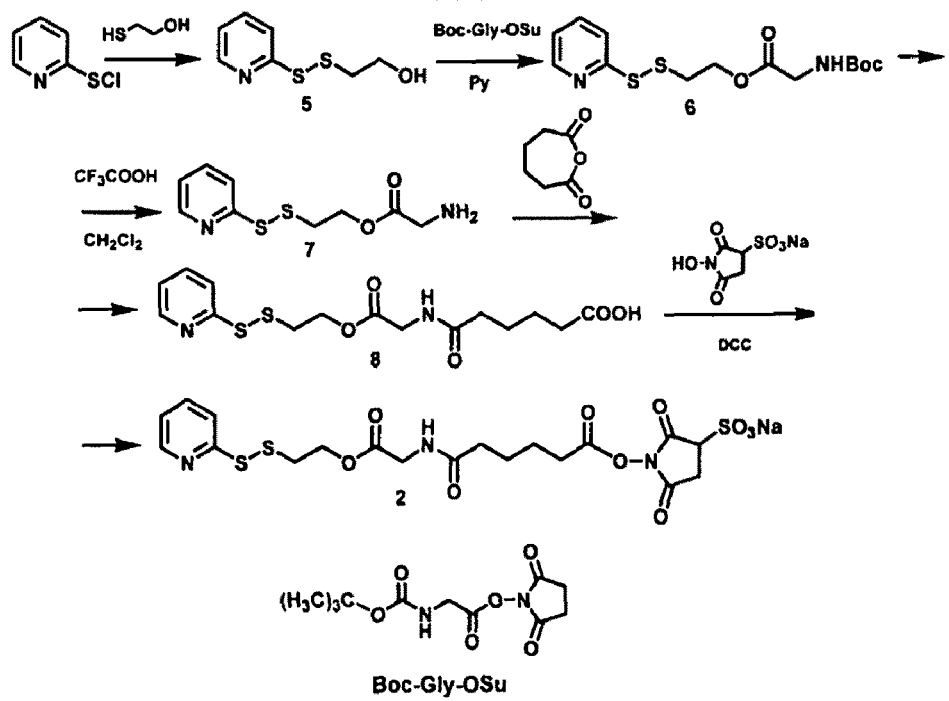
FIG. 3 is a scheme depicting the synthesis of the biodegradable cross-linker 2.

To synthesize the cross-linker 2, β-mercaptoethanol was reacted with 2-pyridine sulfenyl chloride (freshly prepared from 2,2'-dipyridyldisulfide and $Cl_2$), and the resulting 2-(2-pyridyldithio)ethanol 5 was esterified with Boc-Gly-OSu. The resulting Boc-glycine ester 6 was deprotected to the amine 7, which was acylated with adipic anydride, forming the acid 8. Finally, the cross-linker 2 was prepared analogously to the cross-linker 1 (see FIG. 3). 2-(2-Pyridyldithio) ethanol 5.

2,2'-Dipyridyldisulfide (Sigma-Aldrich, 2.50 g, 11.35 mmol) was suspended in dry pentane (150 ml) and saturated with $Cl_2$ for 20 min. at 17-20° C. under vigorous stirring. The resulting thick suspension of 2-pyridine sulfenyl chloride was evacuated at 15 mm Hg until dryness, the residue was protected with argon, and anhydrous acetic acid (39 ml) was added. Under the continuing Ar-protection, a solution of β-mercaptoethanol (1.05 ml) in anhydrous acetic acid (12 ml) was added dropwise in 15 min. at 18-20° C. into the stirred mixture. The stirring was continued for 5 min., and water (25 ml) was added. The reaction solution was dried in vacuo to a syrup (6.66 g), and a solution of $KHCO_3$ (11 g) in water (65 ml) was added. The reaction products were extracted with CHCl3 (2×50 ml), the organic layer was dried over $Na_2SO_4$, filtered from the desiccant and the solvent was removed in vacuo. The crude compound 5 (3.59 g) was purified by flash-chromatography on silica-gel, elution with mixtures of hexane and ethyl acetate (5:1 to 1:1 by volume). Yield of pure compound 5 was 2.58 g (92%). TLC of 5 (heptane-ethyl acetate, 2:3): one spot, $R_f$ ca. 0.4. $^1H$ NMR of compound 5 ($CDCl_3$), δ, ppm: 2.93 (t, 6 Hz, 2H), 3.77 (br. m, 2H), 5.75 (br. m, 1H), 7.13 (m, 1H), 7.38 (m, 1H), 7.56 (m, 1H), 8.49 (m, 1H).

Boc-Protected Glycine Ester 6.

The alcohol 5 (0.818 g, 4.36 mmol) and Boc-glycine N-hydroxysuccinimide ester (Boc-Gly-OSu) (Sigma-Aldrich, 1.835 g, 6.45 mmol) in dry pyridine (3.5 ml) were stirred at 55-65° C. for 1 h. The reaction mixture was diluted with toluene (30 ml) and dried in vacuo. The residue (3.28 g) was dissolved in ethyl acetate (40 ml), diluted with hexane (100 ml), filtered and washed with 10% NaCl (50 ml). The organic layer was dried over $Na_2SO_4$, filtered from the desiccant and dried in vacuo. The crude compound 6 (1.80 g) was purified by flash-chromatography on silica-gel, elution with mixtures of hexane and ethyl acetate (5:1 to 1:1 by volume). Yield of pure compound 6 was 1.41 g (94%). TLC of compound 6 (heptane-ethyl acetate, 2:3): one spot, $R_f$ ca. 0.7. $^1H$ NMR of compound 6 ($CDCl_3$), δ, ppm: 1.42 (s, 9H), 3.02 (t, 7 Hz, 2H), 3.88 (d, 6 Hz, 2H), 4.38 (t, 7 Hz, 2H), 4.98 (br., 1H), 7.08 (m, 1H), 7.60-7.66 (m, 2H), 8.45 (m, 1H).

Pyridyldithio-Carboxylic Acid 8.

Compound 6 (1.431 g, 4.1 mmol) was dissolved in $CH_2Cl_2$ (10 ml), and $CF_3COOH$ (5 ml) was added. The mixture was left at ambient temperature for 2 h. The volatiles were removed in vacuo, the residual trifluoroacetate of amine 7 (3.59 g) was dissolved in a mixture of $CH_2Cl_2$ (10 ml) with pyridine (5 ml), and cooled in an ice bath. Adipic anhydride (1.86 g, 14.5 mmol) was added dropwise in 1 min., the mixture was stirred for 10 min. in the cooling bath and for 0.5 h at room temperature. The solvents were removed in vacuo, the residual syrup was diluted with water (40 ml), neutralized with $KHCO_3$ (4.0 g), vacuum-concentrated to 30 g (to remove pyridine) and acidified with $H_3PO_4$ to pH=3. The acid 8 was extracted with $CHCl_3$ (2×30 ml), the extact was dried over $Na_2SO_4$, and the solvent was removed in vacuo. The crude compound 8 (2.35 g) was dissolved in water (60 ml) in the presence of $KHCO_3$ (3.0 g), the non-acidic impurities were extracted with a mixture $CHCl_3$—hexane (3:1 by volume, 60 ml), and the aqueous phase was acidified with $H_3PO_4$ to pH=4. After extraction with $CHCl_3$ (2×45 ml), drying over $Na_2SO_4$ and removal of the solvent in vacuo, the residue (1.86 g) was dissolved in ethyl acetate (4 ml) and crystallized by gradual addition of heptane (4 ml). Seeding with crystals of compound 8 assists the crystallization. The crystals were filtered off, washed with ethyl acetate-heptane (1:1, 10 ml), with hexane (10 ml) and dried in vacuo. Yield of pure crystalline compound 8 was 1.31 g (85%). TLC of compound 8 ($CHCl_3$-2-propanol, 9:1): one spot, $R_f$ ca. 0.4. $^1H$ NMR of compound 8 ($CDCl_3$), δ, PPM: 1.67 (m, 4H), 2.26 (t, 6 Hz, 2H), 2.35 (t, 6 Hz, 2H), 3.02 (t, 7 Hz, 2H), 4.00 (d, 6 Hz, 2H), 4.39 (t, 7 Hz, 2H), 6.28 (br. t, 6 Hz, 1H), 7.10 (m, 1H), 7.60-7.80 (m, 2H), 8.45 (m, 1H).

Biodegradable hetero-bifunctional cross-linker 2. The acid 8 (1.284 g, 3.45 mmol), N-hydroxysulfosuccinimide disodium salt (Pierce, 0.700 g, 3.22 mmol) and dicyclohexylcarbodiimide (1.50 g, 4.85 mmol) were reacted in N,N-dimethylacetamide (26 ml) and water (3.0 ml) as described above for the preparation of the cross-linker 1. Isolation and purification of the cross-linker 2 were similar to those of the cross-linker 1. Yield of pure cross-linker 2 was 1.652 g (90%). $^1H$ NMR of the cross-linker 2 (DMSO-de), δ, ppm: 1.61 (m, 4H), 2.18 (t, 6 Hz, 2H), 2.67 (br. t, 6 Hz, 2H), 2.86 (d, 18 Hz, 1H), 3.15 (br., 1H), 3.11 (t, 7 Hz, 2H), 3.82 (d, 6 Hz, 2H), 3.94 (br. d, 1H) 4.26 (t, 7 Hz, 2H), 7.26 (m, 1H), 7.78 (m, 1H), 7.86 (m, 1H), 8.30 (br. t, 6 Hz, 1H), 8.46 (m, 1H).

Surfaces Functionalized to Contain Reactive Groups

The terms "surface", "substrate", "matrix" or "support," as used interchangeably herein, mean any surface treated or functionalized as well as to be treated or functionalized to contain functional groups suitable for attachment of biomaterial via a biodegradable cross-linker of the present invention. Non-limiting examples of such surfaces include metal surfaces, non-metal surfaces having at least one carbon, and combined materials such as, for example, organosylated metals.

In this description, "metal support" denotes a uniform, solid homogenous or heterogeneous material support, or a network of supporting structures suitable for biomaterial delivery in accordance with the present invention. The metal support can be any structure having a metal surface, including devices and preferably medical devices. The term "medical device" means any tool, mechanism, or apparatus that can be used during medical intervention, including but not limited to surgical implants, surgical sutures, and prostheses. Preferably, devices suitable in this invention have spatial dimensions that are at least 0.1 mm. However, smaller dimensions (i.e., below 0.1 mm) are also contemplated.

A device is "implanted" if it is permanently or temporarily placed in contact with a cell or a tissue wherein the whole device or a portion thereof is in contact with a cell or a tissue.

The surface contemplated by the present invention can have any shape or form suitable for variety of purposes such as, for example, a delivery of a biomaterial to an organism. In that, the surface can be an existing medical implant such as, for example, a stent, a cardiovascular valve, or a suture which can be functionalized and then treated to attach a biomaterial. Also, the surface can be first functionalized and then treated to contain the biomaterial before or after being molded into the desired shape. In some of the embodiments, the surface can be in a form of polymeric particles functionalized as described in detail below.

Medical devices appropriate for the biomaterial delivery in the present invention include, but are not limited to, heart valves, wire sutures, temporary joint replacements and urinary dilators. Other suitable medical devices for this invention include orthopedic implants such as joint prostheses, screws, nails, nuts, bolts, plates, rods, pins, wires, inserters, osteoports, halo systems and other orthopedic devices used for stabilization or fixation of spinal and long bone fractures or disarticulations. Other devices may include non-orthopedic devices, temporary placements and permanent implants, such as tracheostomy devices, jejunostomy and gastrostomy tubes, intraurethral and other genitourinary implants, stylets, dilators, stents, vascular clips and filters, pacemakers, wire guides and access ports of subcutaneously implanted vascular catheters and contact lenses. In a preferred embodiment, the surface is a medical device with a stainless steel surface, such as a stent.

Non-limiting examples of other devices useful in this invention include containers, platforms or plates which can be used, for example, for research or diagnostic purposes.

Examples of methods of functionalizing surfaces for use in the present invention are described further below.

Metal Surfaces

A metal support can be functionalized with a monomeric or polymeric surface modifier having chemical moieties that bind to the metal as described in U.S. Patent Application Publication No. 2003/0044408A1 by Levy et al., filed on Jun. 14, 2002 and incorporated herein in its entirety. Illustrative of suitable metallic materials are stainless steel, MP35 stainless steel, aluminum oxide, platinum, platinum alloys, elgiloy, tivanium, vitallium, titanium, titanium alloys, NITINOL (nickel-titanium alloy), chromium, cobalt, their alloys and oxides.

A surface modifier suitable for functionalizing a metal support is any compound that (i) can chemically coordinate with a metal surface and (ii) has a reactive group which is a chemical group adapted to covalently react with a substrate-reactive end group of a biodegradable cross-linker.

Examples of such surface modifiers include but are not limited to polybisphosphonates, and polyamines, preferably polyaminobisphosphonates. Other surface coordinating compounds with side functionalities for branching attachment and amplification, include any polymeric, oligomeric, or monomeric compound that contains groups capable of coordination to metal ions (e.g., chelating groups) such as phosphonic groups, hydroxamic groups, carboxylic groups, sulfonic residues, sulfinic groups and amino groups.

The reactive group of the surface modifier for metal surfaces is a chemical group adapted to covalently react with a substrate-reactive end group of a biodegradable cross-linker. Non-limiting examples of the reactive group include amino or thiol groups (also in latent modifications, e.g., alkyldithio groups, which can be reduced to thiol groups immediately before the use), alkylating groups (maleimido, vinylsulfonyl, epoxy or iodoacetamido groups), and other groups suitable for the covalent attachment of other reactive groups and at the same time, comparatively inert towards the coordination with the metal ions on the surface.

The polymeric backbone of the polymeric surface modifiers should be sufficiently stable in the aqueous surrounding, and can be represented by a chain consisting purely of carbon atoms (e.g., polymers based on polyallylamine), or could incorporate heteroatoms (oxygen nitrogen, etc.) into the polymeric chain (e.g., polylysine, also with a part of lysine residues modified to insert chelating groups for better coordination to the metal). The polymeric surface modifier can be derived from a polyamine or other polymers. For example, it could be a polymer with pendant phosphonate or geminal bisphosphonate groups (for coordination with the metal ions on the surface) and alkyldithio groups as latent thiol functions for the subsequent reactions.

A chelating group can be a chemical entity consisting of several units capable of coordination to the metal ions and positioned in close proximity to each other, so they could simultaneously bind the same metal ion, thus increasing the strength of the interaction. Chelating groups could contain units capable of forming only metal-oxygen coordination bonds with the metal ions (geminal bisphosphonate, geminal or vicinal dicarboxylate, or hydroxamate), or they also could involve other atoms (e.g., iminodiacetate group, which in addition to the metal-oxygen bonds can also form metal-nitrogen bonds involving the tertiary amino group).

Coordination to the metal surface usually depends on pH and is suppressed in both strongly acidic and strongly alkaline media. Stronger chelators (e.g., geminal bisphosphonate groups) could be used in wide regions of pH (from approximately 2 to 12), whereas amino groups are much weaker towards the coordination with the metal surface, and probably, would be effective only in a narrow region of pH close to the value of $pK_a$ characteristic to them (ca. 10 for the aliphatic amino groups). These groups, alone or in combinations, would be suitable for coordination chemistry-based surface modifications. Preferably, the surface modifier is a polyamine, a polyaminobisphosphonate, polylysine or polyallylamine.

For example, the metal surface can be treated with either polyallylaminobisphosphonate (PAABP) or poly-bisphosphonates containing latent thiol groups to form a chemosorption layer with binding through coordination of the bisphosphonate groups. If PAABP is used, the primary amino groups of the PAABP chemosorption layer can be transformed into latent thiol groups, which then can be used for the attachment of the biodegradable cross-linker of the invention.

It is also possible to amplify the number of reactive functionalities attached to the chemosorption layer by using several variants of expansion chemistry. Thus, using an amplifier, a number of reactive functionalities can be controlled. One such variant is the reaction of thiol groups present on the chemosorption layer with a polymer containing multiple thiol-reactive groups, such as, for example, (poly)ethylenimine (PEI) modified with 2-pyridyldithio-groups (PDT-groups) (PEI-PDT), which are then treated with a reducing agent to form thiol groups (see Example 1).

For example, pyridyldithio groups rapidly react with thiols in both aqueous (pH 5 to 8) and non-aqueous media, forming stable disulfide linkages. By using a large excess of the PAA-pyridyldithio polymers, most of pyridyldithio groups of the amplification polymer will remain unreacted, and can be later reduced to form thiol-groups. The polymers with multiple pyridyldithio groups can be prepared from reactions of SPDP with polymeric amines such as polyallylamine and polyethylene imine. These polyamines, in their "free base" form, can easily dissolve in non-aqueous solvents (dichloromethane or a mixture of dichloromethane and isopropanol) and smoothly react with SPDP at 0-20° C. The reactions are typically complete in less than 30 min., and no side-reactions (hydrolysis of succinimidyl ester, or degradation of pyridyldithio group) occur. Modified polymers prepared in this manner can be purified from non-polymeric impurities (N-hydroxysuccinimide, and sometimes, an excess of SPDP) by extraction with suitable solvents (e.g., methanol or isopropanol).

Non-Metal Surfaces Having at Least One Carbon

The preferred non-metal surfaces having at least one carbon are polymeric surfaces. The polymeric surfaces of the invention can be biodegradable and non-biodegradable. Non-limiting examples of the polymeric surfaces used in the invention are polyurethane, polyester, polylactic acid, polyglycolic acid, poly(lactide-co-glycolide), poly($\epsilon$-caprolactone), polystyrene, polyamide, rubber, silicone rubber, polyacrylonitrile, polyacrylate, and polymetacrylate, poly(alpha-hydroxy acid), poly(dioxanone), poly(orthoester), poyesher-ester), poly(lactone), mixtures thereof and copolymers thereof.

The surfaces comprising at least one carbon (e.g., polymeric surfaces) can also be functionalized by using, for example, a surface modifier comprising a photo-activatable group and a desired reactive group, wherein the photo-activatable group will covalently bind the modifying agent to the surface leaving the desired reactive group pending from the surface.

The term "photo-activatable group" used herein denotes chemical groups capable of generating active species such as free radicals, nitrenes, carbenes and excited states of ketones upon absorption of external electromagnetic or kinetic (thermal) energy. These groups may be chosen to be responsive to various portions of the electromagnetic spectrum, i.e., the groups responsive to ultraviolet, visible and infrared portions of the spectrum. The preferred photo-activatable groups are benzophenones, acetophenones and aryl azides. Upon excitation, photo-activatable groups are capable of covalent attachment to surfaces comprising at least one carbon such as polymers.

One example of such surface modifier is a water-soluble photo-activatable polymer as described in PCT application Serial No. PCT/US04/011861 entitled "MAGNETICALLY CONTROLLABLE DRUG AND GENE DELIVERY STENTS" by inventors, filed on Apr. 16, 2004 and U.S. application Ser. No. 11/250,877, filed on Oct. 14, 2005, a continuation of the PCT application which is incorporated herein in its entirety. The water-soluble photo-activatable polymer is based on a polymer precursor and also comprises the following groups covalently attached to the polymeric precursor: a photo-activatable group, a desired reactive group, and a hydrophilic group.

In certain embodiments of the invention, the polymeric precursor comprises at least one monomer selected from the group consisting of allylamine, vinylamine, acrylic acid, carboxylic acid, alcohol, ethylene oxide, and acyl hydrazine. Preferably, the polymer precursor is polyallylamine. In certain embodiments of the invention, the polyallylamine has a molecular weight of about 200 KDa to about 5 KDa. In the preferred embodiment, the molecular weight is from 70 KDa to 15 KDa.

The reactive group of the water-soluble photo-activatable polymer is a chemical group adapted to covalently react with a substrate-reactive end group of a biodegradable cross-linker. Non-limiting examples of the reactive group are an amino group (primary or secondary), a thiol reactive group, a carboxy group, a thiol group, a protected thiol group, an acyl hydrazine group, an epoxy group, an aldehyde group, and a hydroxy group. Preferably, the thiol-reactive group is selected from the group consisting of a 2-pyridyldithio group, a 3-carboxy-4-nitrophenyldithio group, a maleimide group, an iodoacetamide group, and a vinylsulfonyl group.

The hydrophilic group of the water-soluble photo-activatable polymer of the invention is present in an amount sufficient to make the water-soluble photo-activatable polymer soluble in water. In certain embodiments of the invention, the hydrophilic group is an amino group or a carboxy group.

The reactive group and the hydrophilic group of the water-soluble photo-activatable polymer of the invention can be identical or different. In one embodiment of the invention, both the reactive group and the hydrophilic group are amino groups. In another embodiment of the invention, the reactive group is the 2-pyridyldithio group, and the hydrophilic group is the carboxy group.

In certain embodiments of the invention, the photo-activatable group is an aryl ketone or an aryl azide. Preferably, the aryl ketone is benzophenone or acetophenone.

The water-soluble photo-activatable polymer may have one or more photo-activatable groups. In certain embodiments, the water-soluble photo-activatable polymers have at least one photo-activatable group per molecule. Preferably, the water-soluble photo-activatable polymers have a plurality of photo-activatable groups per molecule. More preferably, photo-activatable groups modify at least 0.1% of monomeric units of a polymer precursor, even more preferably at least 1%, and most preferably from about 20 to about 50%.

The irradiation source can be any source known in the art capable of emitting the light having a wavelength absorbable by the photo-activatable group of the invention. A UV-lamp is preferred when the benzophenone is used as the photo-activatable group.

The term "water-soluble polymer" as used in this disclosure means that the water-soluble photo-activatable polymer of the invention can be diluted with water to at least 1 wt % and preferably to at least 0.1 wt % to form a single phase at a temperature of 20° C., provided that water is essentially free of an organic co-solvent.

In one embodiment of the invention, the water-soluble polymer is polyallylamine based benzophenone (PAA-BzPh) and is represented by a formula:

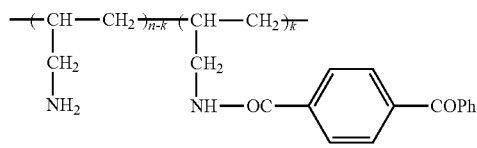

wherein n is 50 to 2000 and k is 10 to 1000.

In another embodiment of the invention, the water-soluble polymer is polyallylamine based benzophenone further modified to contain 2-pyridyldithio groups (PDT-BzPh) and is represented by a formula:

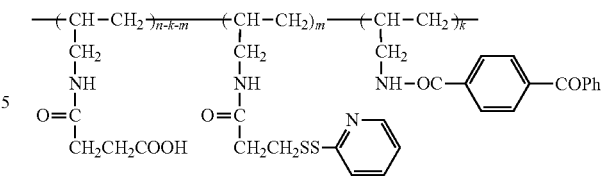

wherein n is 50 to 2000, k is 10 to 1000, and m is 10 to 1000.

Upon excitation of photo-activatable groups, the water-soluble polymer covalently binds to the surface and forms a monomolecular layer on the surface.

The term "layer" used herein means a contiguous or a non-contiguous deposit formed by a covalent bonding of polymers of the invention to the surface. Preferably, the layer is highly homogeneous and pure in that it consists essentially of the water-soluble polymer.

Biomaterial

The biomaterial of the present invention can be any molecule or macromolecule having a suitable reactive group, such as a carboxy (—COOH), amino (—NH$_2$) or thiol group (—SH). For example, proteins or peptides that have been modified to comprise a thiol group or comprise an amino group can be used. A reaction between a thiol-reactive group (2-pyridyldithio, maleimide, etc.) attached to one protein molecule with a thiol group of another protein molecule (or other biomolecule) is widely used for preparation of protein conjugates (See Greg T. Hermanson, Bioconjugate Techniques, Academic Press, San Diego 1996). Reaction of a thiol group with most of the thiol-reactive groups (particularly 2-pyridyldithio group) is very selective and fast in aqueous media at mild conditions. Proteins can be thiolated using a partial reduction of disulfide bridges or via thiolation of lysine residues with a variety of reagents (see Hermanson, pp. 57-70). Preferred is a biomaterial having a thiol-reactive group, preferably an amino group which is capable of reacting with a biomaterial reactive group of the biodegradable cross-linker.

The biomaterial also has therapeutic utility. Suitable biomaterials include nucleic acid sequences, such as transposons, signaling proteins that facilitate wound healing, such as TGF-β, FGF, PDGF, IGF and GH proteins that regulate cell survival and apoptosis, such as Bcl-1 family members and caspases; tumor suppressor proteins, such as the retinoblastoma, p53, PAC, DCC. NFI, NF2, RET, VHL and WT-1 gene products; extracellular matrix proteins, such as laminins, fibronectins and integrins; cell adhesion molecules such as cadherins, N-CAMs, selectins and immunoglobulins; anti-inflammatory proteins such as Thymosin beta-4, IL-10 and IL-12.

In certain embodiments, the biomaterial includes at least one of heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof, a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; a remodeling inhibitor; deoxyribonucleic acid, an antisense nucleotide or another agent for molecular genetic intervention; methotrexate or another antimetabolite or antiproliferative agent; tamoxifen citrate, TAXOL™ or derivatives thereof, or other anti-cancer chemotherapeutic agents; dexamethasone, dexamethasone sodium phosphate, dexamethasone acetate or another dexamethasone derivative, or another anti-inflammatory steroid or non-steroidal anti-inflammatory agent; cyclosporin or another immunosuppressive agent; trapidal (a PDGF antagonist), angiogenin, angiopeptin (a growth hormone antagonist), a growth factor or an anti-growth factor antibody, or another growth factor antagonist; dopamine, bromocriptine mesylate, pergolide mesylate or another dopamine agonist; radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a $^{14}$C-, $^{3}$H-, $^{32}$P- or $^{36}$S-radiolabelled form or other radiolabelled form of any of the foregoing; a hormone; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an igG2 Kappa antibody against Pseudomonas aeruginosa exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs, or a mixture of any of these. The biomaterial can also be selected from cell adhesion molecules belonging to several major receptor families such as, for example, integrins, cadherins, the immunoglobulin superfamily, hyaluronate receptors and mucins and their ligands.

Additionally, the biomaterial can be either component of any affinity-ligand pair. Examples of such affinity ligand pairs include avidin-biotin and IgG-protein A. Furthermore, the biomaterial can be either component of any receptor-ligand pair. One example is transferrin and its receptor. Other affinity ligand pairs include powerful hydrogen bonding or ionic bonding entities such as chemical complexes. Examples of the latter include metallo-amine complexes. Other attractive complexes include nucleic acid base pairs that can immobilize oligonucleotides of a specific sequence, especially antisense. Nucleic acid decoys or synthetic analogues can also be used as pairing agents to bind a designed gene vector with attractive sites. Furthermore, DNA binding proteins can also be considered as specific affinity agents; these include such entities as histones, transcription factors, and receptors such as the glucocorticoid receptor.

In one preferred embodiment, the biomaterial is an antinucleic acid antibody. The antibody can therefore specifically bind a nucleic acid, which encodes a product (or the precursor of a product) that decreases cell proliferation or induces cell death, thereby mitigating the problem of restenosis in arteries and other vessels. The nucleic acid that is tethered to a support via the antibody can efficiently transfect/transducer cells. In general terms, the field of "gene therapy" involves delivering into target cells some polynucleotide, such as an antisense DNA or RNA, a ribozyme, a viral fragment, or a functionally active gene, that has a therapeutic or prophylactic effect on the cell or the organism containing it. Culver, 1994, GENE THERAPY: A HANDBOOK FOR PHYSICIANS (Mary Ann Liebert, Inc., New York, N.Y.). The antibody of the composition can be a full-length (i.e., naturally occurring or formed by normal immunoglobulin gene fragment recombinatorial processes) immunoglobulin molecule (e.g., an IgG antibody, or IgM or any antibody subtype) or an immunologically active (i.e., specifically binding) portion of an immunoglobulin molecule. The antibody comprises one or more sites which specifically bind with a nucleic acid (i.e., which does not substantially bind other types of molecules). The binding site can be one which binds specifically with a nucleic acid of a desired type without regard to the nucleotide sequence of the nucleic acid. The binding site can, alternatively, be one which binds specifically only with a nucleic acid comprising a desired nucleotide sequence. Preferably, the antibody is a thiol-modified antibody.

The complex formed between a polynucleotide and a cognate antibody can be immobilized on a variety of surfaces such that, when the surface is exposed to a physiological environment in situ, the attached polynucleotide is released, over time, in a manner that enhances delivery of the polynucleotide to cells in the proximity. Surprisingly, DNA transfer by way of immunospecific tethering maintains the nucleic acid in regions that are subject to gene therapy.

Examples of suitable antibodies include Fv, F(ab), and F(ab')$_2$ fragments, which can be generated in conventional fashion, such as by treating an antibody with pepsin or another proteolytic enzyme. The nucleic acid-binding antibody used in a composition of the present invention can be a polyclonal antibody or a monoclonal antibody. A "monoclonal" antibody comprises only one type of antigen binding site that specifically binds with the nucleic acid. A "polyclonal" antibody can comprise multiple antigen binding sites that specifically bind the nucleic acid. An antibody employed in this invention preferably is a full-length antibody or a fragment of an antibody, such as F(ab')$_2$, that possesses the desired binding properties.

A nucleic acid for use in the present invention can be any polynucleotide that one desires to transport to the interior of a cell. In this context, a "therapeutic polynucleotide" is a polymer of nucleotides that, when provided to or expressed in a cell, alleviates, inhibits, or prevents a disease or adverse condition, such as inflammation and/or promotes tissue healing and repair (e.g., wound healing). The nucleic acid can be composed of deoxyribonucleosides or ribonucleosides, and can have phosphodiester linkages or modified linkages, such as those described below. The phrase "nucleic acid" also encompasses polynucleotides composed of bases other than the five that are typical of biological systems: adenine, guanine, thymine, cytosine and uracil.

A suitable nucleic acid can be DNA or RNA, linear or circular and can be single-or-double-stranded. The "DNA" category in this regard includes: cDNA; genomic DNA; triple helical, supercoiled, Z-DNA and other unusual forms of DNA; polynucleotide analogs; an expression construct that comprises a DNA segment coding for a protein, including a therapeutic protein; so-called "antisense" constructs that, upon transcription, yield a ribozyme or an antisense RNA; viral genome fragments, such as viral DNA; plasmids and cosmids; and a gene or a gene fragment.

The nucleic acid also can be RNA, for example, antisense RNA, catalytic RNA, catalytic RNA/protein complex (i.e., a "ribozyme"), and expression construct comprised of RNA that can be translated directly, generating a protein, or that can be reverse transcribed and either transcribed, or transcribed and then translated, generating an RNA or protein product, respectively; transcribable constructs comprising RNA that embodies the promoter/regulatory sequence(s) necessary for the generation of DNA by reverse transcription; viral RNA; and RNA that codes for a therapeutic protein, inter alia. A suitable nucleic acid can be selected on the basis of a known, anticipated, or expected biological activity that the nucleic acid will exhibit upon delivery to the interior of a target cell or its nucleus.

The length of the nucleic acid is not critical to the invention. Any number of base pairs up to the full-length gene may be transfected. For example, the nucleic acid can be linear or circular double-stranded DNA having a length from about 100 to 10,000 base pairs in length, although both longer and shorter nucleic acids can be used.

The nucleic acid can be a therapeutic agent, such as an antisense DNA molecule that inhibits mRNA translation. Alternatively, the nucleic acid can encode a therapeutic agent, such as a transcription or translation product which, when expressed by a target cell to which the nucleic acid-containing composition is delivered, has a therapeutic effect on the cell or on a host organism that includes the cell. Examples of therapeutic transcription products include proteins (e.g., antibodies, enzymes, receptors-binding ligands, wound-healing proteins, anti-restenotic proteins, anti-oncogenic proteins, and transcriptional or translational regulatory proteins), antisense RNA molecules, ribozymes, viral, genome fragments, and the like. The nucleic acid likewise can encode a product that functions as a marker for cells that have been transformed, using the composition. Illustrative markers include proteins that have identifiable spectroscopic properties, such as green fluorescent protein (GFP) and proteins that are expressed on cell surfaces (i.e., can be detected by contacting the target cell with an agent which specifically binds the protein). Also, the nucleic acid can be a prophylactic agent useful in the prevention of disease.

A nucleic-acid category that is important to the present invention encompasses polynucleotides that encode proteins that affect wound-healing. For example, the genes egf, tgf, kgf, hb⁻egf, pdgf, igf, fgf-1, fgf-2, vegf, other growth factors and their receptors, play a considerable role in wound repair.

Another category of polynucleotides, coding for factors that modulate or counteract inflammatory processes, also is significant for the present invention. Also relevant are genes that encode an anti-inflammatory agent such as MSH, a cytokine such as IL-10, or a receptor antagonist that diminishes the inflammatory response.

Polynucleotides coding for anti-restenotic compounds, such as anti-proliferative, anti-migratory, anti-inflammatory and cell-signaling related proteins, are also important to the present invention. These include, but are not limited to, the proteins mentioned in the review of C. E. Appleton and P. A. Kingston, "Gene Therapy for Restenosis—What Now, What Next?," *Current Gene Therapy* 4: 153-182, 2004, (, Tables 2 and 3), which is incorporated herein by reference. In one embodiment the anti-restenotic biomaterial is inducible nitric oxide synthase (iNOS), which may be in the form of adenovirus encoding iNOS.

Suitable polynucleotides can code for an expression product that induces cell death or, alternatively, promotes cell survival, depending on the nucleic acid. These polynucleotides are useful not only for treating tumorigenic and other abnormal cells but also for inducing apoptosis in normal cells. Accordingly, another notable nucleic-acid category for the present invention relates to polynucleotides that, upon expression, encode an anti-oncogenic protein or, upon transcription, yield an anti-oncogenic antisense oligonucleotide. In this context, the phrases "anti-oncogenic protein" and "anti-oncogenic antisense oligonucleotide" respectively denote a protein or an antisense oligonucleotide that, when provided to any region where cell death is desired, or the site of a cancerous or precancerous lesion in a subject, prevents, inhibits, reverses abnormal and normal cellular growth at the site or induces apoptosis of cells. Delivery of such a polynucleotide to cells, pursuant to the present invention, can inhibit cellular growth, differentiation, or migration to prevent movement or unwanted expansion of tissue at or near the site of transfer. Illustrative of this anti-oncogenic category are polynucleotides that code for one of the known anti-oncogenic proteins. Such a polynucleotide would include, for example, a nucleotide sequence taken or derived from one or more of the following genes: abl, akt2, apc, bc12-alpha, bc12-beta, bcl3, bc13, bcl-x, bad, bcr, brcal, brca2, cbl, ccndl, cdk4, crk-ll, csflrlfms, dbl, dcc, dpc4/smad4, e-cad, e2fl/rbap, egfr/erbb-1, elk], elk3, eph, erg, els], ets2, fer, fgr/src2, fos, fps/fes, fral, fra2, fyn, hck, hek, her2/erbb-2/neu, her3/erbb-3, her4/erbb-4, hrasl, hst2, hstfl, ink4a, ink46, int2lfgj3, jun, junb, fund, kip2, kit, kras2a, kras2b, ck, lyn, mas, max, mcc, met, mlhl, mos, msh2, msh3, msh6, myb, myba, mybb, myc, mycll, mycn, nfl, nj2, nras, p53, pdg/b, piml, pmsl, pms2, plc, pten, raft, rbl, rel, ret, rosl, ski, srcl, tall, tgjbr2, thral, thrb, tiaml, irk, vav, vhl, wafl, wntl, wnt2, wil and yesl. By the same token, oligonucleotides that inhibit expression of one of these genes can be used as anti-oncogenic antisense oligonucleotides.

Nucleic acids having modified internucleoside linkages also can be used in composition according to the present invention. For example, nucleic acids can be employed that contain modified internucleoside linkages which exhibit increased nuclease stability. Such polynuclotides include, for example, those that contain one or more phosphonate, phosphorothioate, phosphorodithioate, phosphoramidate methoxyethyl phosphoramidate, formacetal, thioformacetal, diisopropylsilyl, acetamidate, carbamate, dimethylene-sulfide ($—CH_2—S—CH_2—$), dimethylene-sulfoxide ($—CH_2—SO—CH_2—$), dimethylenesulfone ($—CH_2—SO_2—CH_2—$), 2'-O-alkyl, and 2'-deoxy-2'-fluoro-phosphorothioate internucleoside linkages.

For present purposes, a nucleic acid can be prepared or isolated by any conventional means typically used to prepare or isolate nucleic acids. For example, DNA and RNA can be chemically synthesized using commercially available reagents and synthesizers by known methods. For example, see Gait, 1985, in: OLIGONUCLEOTIDE SYNTHESIS: A PRACTICAL APPROACH (IRL Press, Oxford, England). RNA molecules can also be produced in high yield via in vitro transcription techniques, using plasmids such as SP65, available from Promega Corporation (Madison, Wis.). The nucleic acid can be purified by any suitable means, and many such means are known. For example, the nucleic acid can be purified by reverse-phase or ion exchange HPLC, size exclusion chromatography, or gel electrophoresis. Of course, the skilled artisan will recognize that the method of purification will depend in part on the size of the DNA to be purified. The nucleic acid also can be prepared via any of the innumerable recombinant techniques that are known or that are developed hereafter.

A suitable nucleic acid can be engineered into a variety of known host vector systems that provide for replication of the nucleic acid on a scale suitable for the preparation of an inventive composition. Vector systems can be viral or non-viral. Particular examples of viral vector systems include adenovirus, retrovirus, adeno-associated virus and herpes simplex virus. Preferably, an adenovirus vector is used. A non-viral vector system includes a plasmid, a circular, double-stranded DNA molecule. Viral and nonviral vector systems can be designed, using known methods, to contain the elements necessary for directing transcription, translation, or both, of the nucleic acid in a cell to which is delivered. Methods which are known to the skilled artisan can be used to construct expression constructs having the protein coding sequence operably linked with appropriate transcriptional/translational control signals. These methods include in vitro recombinant DNA techniques and synthetic techniques. For instance, see Sambrook et al., 1989, MOLECULAR CLONING: A LABORATORY MANUAL (Cold Spring Harbor Laboratory, New York), and Ausubel et al., 1997, CURRENT PROTOCOLS IN MOLECULAR BIOLOGY (John Wiley & Sons, New York).

A nucleic acid encoding one or more proteins of interest can be operatively associated with a variety of different promoter/regulator sequences. The promoter/regulator sequences can include a constitutive or inducible promoter, and can be used under the appropriate conditions to direct high level or regulated expression of the gene of interest. Particular examples of promoter/regulatory regions that can be used include the cytomegalovirus (CMV) promoter/regulatory region and the promoter/regulatory regions associated with the SV40 early genes or the SV40 late genes. Preferably, the human CMV promoter is used, but substantially any promoter/regulatory region directing high level or regulated expression of the gene of interest can be used.

It also is within the scope of the present invention that the employed nucleic acid contains a plurality of protein-coding regions, combined on a single genetic construct under control of one or more promoters. The two or more protein-coding regions can be under the transcriptional control of a single promoter, and the transcript of the nucleic acid can comprise one or more internal ribosome entry sites interposed between the protein-coding regions. Thus, a myriad of different genes and genetic constructs can be utilized.

Biomaterials of the present invention also include pharmaceuticals, imaging and diagnostic agents.

In certain embodiments of the composition, the biomaterial is a member selected from the group consisting of an antibody, a viral vector, a growth factor, a bioactive polypeptide, a polynucleotide coding for the bioactive polypeptide, a cell regulatory small molecule, a peptide, a protein, an oligonucleotide, a gene therapy agent, a gene transfection vector, a receptor, a cell, a drug, a drug delivering agent, nitric oxide, an antimicrobial agent, an antibiotic, an antimitotic, dimethyl sulfoxide, an antisecretory agent, an anti-cancer chemotherapeutic agent, steroidal and non-steroidal anti-inflammatories, hormones, an extracellular matrix, a free radical scavenger, an iron chelator, an antioxidant, an imaging agent, and a radiotherapeutic agent. Preferably, the biomaterial is an anti-knob antibody, an adenovirus, a DI domain of the Coxsackie-adenovirus receptor (CAR DI), insulin, an angiogenic peptide, an antiangiogenic peptide, avidin, biotin, IgG, protein A, transferrin, and a receptor for transferrin, a cell adhesion molecule and a ligand cell adhesion molecule. In certain embodiments of the process, the biomaterial is a member selected from the group consisting of a nucleic acid, a gene vector, a protein, a peptide, and a cell. Several different biomaterials can be immobilized on the same surface.

Process of Making the Composition

This invention also provides a process of making the composition. The process comprises providing a biodegradable cross-linker, providing a substrate having at least one reactive group, providing the biomaterial, reacting the substrate with the substrate-reactive end group of the biodegradable cross-linker to covalently attach the biodegradable cross-linker portion to the substrate, and reacting the biomaterial with the biomaterial reactive end group of the biodegradable cross-linker and thereby covalently attaching the biomaterial to the biodegradable cross-linker portion to make the composition. A non-limiting example of the process is shown in FIG. 4A. It is not necessary to first react the biomaterial with the cross-linker, however, it seems to be a more convenient order. Thus, in certain embodiments, the step of reacting the biomaterial with the biomaterial reactive end group of the biodegradable cross-linker is conducted prior to or simultaneously with the step of reacting the substrate with the substrate-reactive end group of the biodegradable cross-linker.

In certain embodiments of the process, providing the biodegradable cross-linker and reacting with the biomaterial comprise; providing (i) a first reactant having the biomaterial reactive end group and a first functional end group and (ii) a second reactant comprising (a) the biodegradable cross-linker portion comprising the hydrolyzable bond, (b) a second functional end group capable of reaction with the first functional end group, and (c) a substrate-reactive end group; reacting the biomaterial with the biomaterial reactive end group of the first reactant; and reacting the first functional group with the second functional group to form the biodegradable cross-linker modified biomaterial. In those embodiments, the biodegradable cross-linker is being formed directly on the biomaterial and then the resulting biomaterial/cross-linker combination is being attached to the surface. In one variant of this embodiment, the first reactant is maleimide-(sulfo)succinimidyl ester, maleimide-tresylate or pyridyldithio-(sulfo) succinimidyl ester and the second reactant is dithiol, thiol-methyl sulfide or bis(methyl sulfide).

Conditions such as temperature, buffers and reactive material can be selected based upon the desired structures. Those skilled in the art are able to select these conditions based upon general chemical principles. Non-limiting examples of the process are provided further below in Examples 2-4.

Biomaterial Delivery

Also provided is a process for using the composition of the invention, such as a process for delivery of biomaterial, the process comprising: contacting the composition with the animal cell or the tissue for a period of time sufficient to allow the hydrolyzable bond to hydrolyze and release the biomaterial and thereby delivering the biomaterial to the animal cell or the tissue. A non-limiting example of the process is shown in FIG. 4. Example 5 describes one example of the process.

In certain embodiments of the process, the biodegradable cross-linker of the composition is selected to affect the period of time. As described earlier, the biodegradable cross-linker can hydrolyze faster or slower depending on its design. Thus, the rate of delivery can be controlled by selecting an appropriate biodegradable cross-linker. Also, the amount of the biomaterial attached to the surface can vary depending on the number of reactive groups on the surface and on the biomaterial. The amplification procedure using, for example, PEI-PDT can be used to obtain a surface containing a desired number of reactive groups. Also, when PDT groups are treated to exchange for thiol groups for further reaction with biodegradable cross-linker, a portion of the PDT groups rather than all PDT groups can be modified, thus providing another way of selecting the desired loading with the biomaterial. Using this guidance, the loading with biomaterial can be selected from 100% of available groups to 0.1%. In one variant, the loading was 25%.

The invention will be illustrated in more detail with reference to the following Examples, but it should be understood that the present invention is not deemed to be limited thereto.

EXAMPLES

Example 1

This experiment demonstrated the idea of direct covalent tethering of a biomaterial to stainless steel surfaces using a thiol-cleavable, heterobifunctional cross-linker sulfosuccinimidyl 6-(3'-[2-pyridyldithio]-propionamido)hexanoate (sulfo-LC-SPDP) (Pierce Biotechnology, Inc., Rockford, Ill.).

500 μl of Cy3-labeled adenovirus (Cy3Ad-GFP) (batch 11; $1.3 \times 10^{12}$ particles) were reacted at a room temperature (RT) for 70 min with 15 mg of LC-sulfo-SPDP to form Cy3-labeled DPT modified adenovirus (Cy3Ad-PDT-GFP). The reaction mixture was placed into SLIDE-A-LYZER dialysis cassette with a cut-off of 10 kDa and dialyzed against PBS for 22 hours with 3 changes of PBS. The last portion of PBS was degassed, contained 10 mM of EDTA, and the dialysis was run under the argon atmosphere.

The next day, 9 meshes of 316L steel were pretreated in a standard way (i.e., 15 min exposure to 1 N nitric acid, followed by 15 min exposure to isopropanol, and 5 rinses in double distilled water).

Six of the meshes were incubated for 5 hours in 1.3% solution of PrSSPAABP, a polyallylamine (PAA) modified with 2,2-diphosphonoethyl groups (BP) and propyldithio groups (PrSS) at 60° C., while 3 meshes were incubated in the 3% polyallylamine modified with 2,2 diphosphonoethyl groups (PAABP) for 5 hours at 60° C. Then, the meshes were washed in a double distilled water (DDW), and 6 meshes treated with PrSSPAABP were reacted with Tri(2-carboxyethyl)phosphine (TCEP) (20 mg/ml in 0.1 M acetic buffer) for 25 min at RT. Next, the meshes were washed with acetic buffer and PBS, and 3 of them were reacted with (poly) ethylenimine (PEI) modified with 2-pyridyldithio-groups (PDT-groups) (PEI-PDT) amplifier (high modification, 25% of a total number of ethyleneimine links—0.5 ml, DDW—1.25 ml, 0.4 M acetic buffer—0.25 ml) for 40 min at RT under shaking. The purpose of the amplification procedure was to increase the number of PDT groups on the surface.

The other 3 meshes as well as the 3 meshes incubated with PAABP were reacted in small Eppendorf tubes with 150 pl of dialyzed degassed Cy3-labeled DPT modified adenovirus (Cy3Ad-PDT-GFP) in 4% BSA. Three meshes reacted with amplifier were washed with acetic buffer and PBS and reacted with DTT (20 mg/ml in DDW) for 20 min at RT under shaking. Finally the meshes were washed with PBS and reacted in small Eppendorf tubes with 150 PI of dialyzed degassed Cy3Ad-PDT-GFP in 4% BSA. The conjugation of virus with meshes was allowed to run overnight at RT under shaking for all 3 groups.

In general, the chemical scheme for 3 groups of meshes can be presented as follows:
1. Control: Me-PAABP+(PDT-Ad) (no covalent bond formation)
2. No amplification: (Me-PrSSPAABP+TCEP)-.Me-PAABP-SH+PDT-Ad--+Me-PAABP-Ad
3. PEI amplification: (Me-PrSSPAABP+TCEP)→Me-PAABP-SH+PDT-PEI-i Me-PAABP-PEI-PDT(n)+DTT-+Me-PAABP-PEI-SH(n)+PDT-Ad--+Me-PAABP-PEI-Ad In this general scheme, Cy3Ad-PDT-GFP is abbreviated as PDT-Ad for the ease of reference.

On the next day, the meshes were examined under a fluorescent microscope. Essentially no fluorescence was observed in control samples (group 1), while low-moderate fluorescence was observed with the samples from the group 2, and a moderate-high fluorescence intensity was seen with the samples from the group 3.

On the same day, the meshes were placed into cultures of ca. 60% confluent HEK 293 and A 10 (rat arterial smooth muscle cells) cells. No GFP-positive cells were seen anywhere in the wells 24 hours after mesh placement. Then the medium was changed, and DTT in concentration 40 mg/ml was dissolved in the medium (80 mg/per well). No GFP-positive cells appeared during 5 additional days of incubation. This experiment demonstrates that a non-degradable covalent linker such as sulfo-LC-SPDP prohibits adenovirus transduction.

Example 2

This experiment was carried out to examine a strategy of covalent Ad binding to steel surface using cleavable (hydrolysable) N-succinimidyl 3-(2-pyridyldithio)-propionate (SPDP) cross-linker with protracted kinetics of hydrolysis. Twelve meshes of 316L steel were pretreated in a standard way, and 8 of them were reacted in 1% PrSSPAABP for 5 hours at 60° C. Four control (no thiol group on PAABP so no covalent bond with Ad) meshes were reacted with 3% polyallylamine modified with 2,2-diphosphonoethyl groups (PAABP) for 5 hours at 60° C. The meshes were washed, and the PrSSPAABP-treated specimens were reacted with TCEP (20 mg/ml in 0.1 M acetic buffer) for 25 min at RT under shaking. After TCEP cleavage the meshes were washed in DDW and reacted with PEI-PDT amplifier (0.5 ml, DDW 1.25 ml, 0.4M acetic buffer 0.25 ml) for 1 hour. Then the meshes were washed with acetic buffer and DDW and were reacted with DTT (20 mg/ml in DDW) for 20 min at RT under shaking.

In parallel, 750 μl of Cy3AdGFP (batch 14) were reacted with 30 mg of the cleavable SPDP analogue, a biodegradable cross-linker 1 (see FIG. 1A) for 1 hour at RT under shaking. The modified virus was purified using desalting column (Ultragel A6) primed with degassed PBS/EDTA.

The activated virus was then reacted with thiolated meshes and with control meshes in 5% BSA/degassed PBS overnight. The next day the meshes were examined under fluorescence microscope. Both controls and properly conjugated meshes demonstrated Cy3Ad presence. However, the amount of associated Ad was much higher for properly conjugated meshes (the term "properly conjugated" means the situation wherein Ad is actually covalently bound to the mesh via thiol groups of reduced PrSSPAABP). This control was performed to assess the non-specific binding component in the overall virus binding to the meshes.

The meshes were placed into confluent HEK 293 and 30% confluent A10 cell cultures and the transduction was examined after 24 hours. No transduced cells were seen in controls and properly conjugated samples placed in HEK 293 and A 10 cells. Thus, prolonged linker hydrolysis kinetics does not enable adenovirus transduction using the amount of the linker used in this example.

Example 3

This experiment was carried out to explore a strategy using covalent Ad binding to steel surface using cleavable (hydrolysable) SPDP cross-linker with a rapid kinetics of hydrolysis. Twelve stainless steel meshes (316 L) were cleaned with isopropanol and 1N nitric acid and incubated for 3.5 hours in 1.5% PrSSPAABP at 80° C. under intensive shaking. The meshes were washed with DDW and reacted with TCEP (30 mg/ml; in 0.1 M acetic buffer) for 30 min at RT under shaking. After successive washings with acetic buffer and water the meshes were reacted with PEI-PDT for 90 min at 42° C. under intensive shaking. Next the meshes were washed with PBS and reacted with DTT (25 mg/ml in DDW) for 30 min under intensive shaking.

In parallel, 1 ml of Ad-GFP (in-house batch, $2.25 \times 10^{12}$/ml) was diluted with 0.5 ml of carbonate/bicarbonate buffer (pH=9.3). 12.2 mg of rapidly hydrolyzable crosslinker 2 (see FIG. 1B) were dissolved in 1 ml of PBS and 64 µl of this solution were added to Ad suspension. Additionally 1 mg of Cy3-NHS dye was dissolved in 1 ml of carbonate/bicarbonate buffer and 2001 µl of this dilution were added to the reaction mixture. The reaction was allowed to run under moderate shaking for 40 min at RT and additionally for 30 min at 4° C. Then the Ad was gel-filtered using Ultragel A6 into degassed PBS/EDTA, and the virus-containing fractions (5-7.5 ml) were pooled and bubbled with argon. 1 ml of double-modified Ad was diluted by 1 ml of degassed PBS and reacted with the meshes in argon atmosphere at 22° C. under intensive shaking (240 rpm) for 14 hours.

The next day, the meshes were studied under a fluorescent microscope, and intensive surface labeling indicating virus binding was noted whereas free double modified Ad possessed very faint fluorescence. Surprisingly, Ad layer on the surface was quite resistant to abrasion since fluorescence was largely retained when the mesh was rubbed with water-soaked latex glove.

Two meshes were placed into HEK 293 cell cultures, and 4 meshes were placed into A 10 cell cultures. The remaining 4 meshes were individually placed into Eppendorf tubes in 250 µl of PBS, and the tubes were shaken at RT (n=2) or at 4° C. (n=2) for 68 hours.

Eighteen hours after mesh placement, intensive localized transduction was observed in both HEK 293 and A10 cultures. The meshes from A10 cultures were then transferred to the fresh cell cultures, and intense de novo transduction was noticed after 18 hours (not shown), indicating that the persistent viable vector was still present.

The meshes that were slated for in vitro "release" experiments were analyzed 68 hours after commencement of incubation. The meshes incubated at 4° C. preserved higher amount of Cy3-labeled Ad, than the counterparts processed at room temperature. This observation is in accordance with the presumed mechanism of release based on hydrolysis of the cross-linker that attaches Ad to the steel surface.

Example 4

Nine meshes were pretreated with isopropanol and 1 N nitric acid and incubated for 3 hours in 2% solution of PrSS-PAABP at 70° C. under intensive shaking (250 rpm). Next the meshes were reacted for 25 min with TCEP (20 mg/ml in 0.1 M acetic buffer) at 30° C. under shaking. After washing the meshes were reacted with PEI-PDT for 1 hour at 30° C. under intensive shaking. The meshes were washed and reacted under the same conditions with DTT (20 mg/ml in water) for 30 min. Finally, the washed meshes were reacted for 2 hours with 0.5 ml of Ad-GFP modified by rapidly cleavable cross-linker 2 at 30° C. under 250 rpm shaking.

Briefly, 350 µl of a new Ad-GFP batch (5e12/ml) were diluted with 350 Id of carbonate/bicarbonate buffer (pH 9.3) and 75 µl of 12.2 mg/ml of rapidly hydrolizable cross-linker 2 solution in PBS was added. The modification was carried out for 30 min at RT and finally the reaction mixture was gel filtered through the Ultragel A 6. The fractions 5-8 ml were pooled and used for conjugation.

The washed meshes were placed in confluent A10 (n=6) and HEK 293 (n=3) monolayers. The cultures were photographed and analyzed with subsequent fluorimetry after 20 and 72 hours.

The results with A10 and HEK (FIG. 5) clearly show that GFP transduction sharply increases between 20 and 72 hours (ca 10-fold for A10), which is not the case for affinity adapter-mediated virus-tethering systems. These results suggest that Ad release occurs due to linker hydrolysis (the latter have ti/2 of 26 days at RT).

Example 5

Six stainless steel Velocity™ stents (Cordis Corp) were cleaned with isopropanol, THF, chloroform (2 hours at 55° C.), 1 N nitric acid (1 hour) and heated to 260° C. for 1 hour. Then the stents were crimped on catheters and reacted with a 2% aqueous solution of PrSSPAABP for 4 hours at 58° C. at 250 rpm. Next, the samples were reduced with TCEP (25 mg/ml in 0.1 M acetic buffer) for 25 min at 40-35° C. and 250 rpm. After washing, the stents were reacted overnight at 28° C. 250 rpm with the PEI-PDT amplifier.

Next, the samples were washed in acetate buffer and PBS and reacted with DTT 16 mg/ml, 28° C., 250 rpm for 25 min. In parallel 350 µl of Ad-GFP (5e12/ml) were diluted with 350 µl of carbonate/bicarbonate buffer (pH 9.3) and 75 µl of 12.2 mg/ml of rapidly hydrolysable crosslinker 2 solution in PBS was added. The modification was carried out for 30 min at RT and finally the reaction mixture was gel filtered through the Ultragel A6. The fractions (5-8 ml) were pooled. Stents washed following DTT step were exposed to the Ad/cross-linker mixture for 5 hours at 28° C. at 250 rpm.

Six rats received stent implants using the established method with a TEFLON tubing protecting sheath. The animals were sacrificed on the day 4 after the stent deployment. Stented arterial segments were retrieved following formalin perfusion-fixation. The stents were removed and the arteries were washed in PBS and embedded into an optimal cutting temperature compound (a mixture of PVA and PEG commonly used in histology for cryoblocks preparation). The blocks were cut, and arterial sections were either directly examined by fluorescent microscopy or were immunostained using anti-GFP antibody. Intensive GFP expression was observed in media and adventitia of stented arterial segments three days following stent deployment in all six animals.

Example 6

The present experiment was designed to investigate the release rate of Ad directly tethered to polybisphosphonate-modified stainless steel meshes. Two different hydrolysable cross-linkers with slow and rapid kinetics of hydrolysis (i.e., the cross-linker 1 (SHC) and the cross-linker 2 (RHC), respectively) as described in Examples 2 and 3 were employed. Additionally, modification of Ad by RHC was carried out at 2 different concentrations of cross-linker. To visualize surface-attached Ad and make possible fluorimetric and microscopic assessment, Ad was co-modified with cross-linkers and fluorescent tag, Cy3.

The release of surface-bound Ad can occur only after breakdown of all hydrolysable bonds connecting it to the surface. Since a $t_n$ of each individual ester bond in the cross-linker is a constant and is significantly higher for the RHC, it is expected that 1) the increase of the crosslinker concentration will slow the release rate of Ad due to the prolongation of the time period needed for the hydrolysis of all cross-linker molecules holding the individual virus particle, and 2) the release rate will be faster for the Ad modified with RHC in comparison to SHC-treated Ad.

To study the release, two fluorescence-based methods were employed, the supernatant method and the surface associated fluorescence method as described below.

Supernatant Method

The virus-conjugated stainless steel meshes were individually placed in a leaching solution (PBS/0.06% Tween-20) at 37° C. At predetermined time points, the supernatants were collected, and fresh PBS/0.06% Tween-20 was added. The amount of Cy3-labeled Ad in the supernatants was determined by fluorimetry.

Surface Associated Fluorescence Method

Immediately after the virus conjugation, the surface of the meshes was studied by fluorescence microscopy and the images of four random low power fields for each mesh were acquired using standardized settings of microscope and camera. The meshes were then placed in PBS/0.06% Tween-20. The images were taken again at the predetermined time points (simultaneously with buffer change and supernatant sampling). The digital images were analyzed using mean luminescence intensity of Adobe Photoshop-generated histograms for the quantification of a surface-attached Ad.

Fourteen 1.25 cm×1.25 cm stainless steel meshes were flattened using Carver press, weighed, cleaned with isopropanol and nitric acid, and reacted individually in solution of either 1% PrSSPAABP (N=12) or 1.5% PAABP (N=2, control) for 3.5 hours (72° C., 200 rpm). After extensive DDW washes, the PrSSPAABP-treated specimens were exposed to TCEP (20 mg/ml in 0.1 M acetic buffer; 37° C., 200 rpm) for 25 min. The meshes were then washed and reacted with PEI-PDT amplifier (90 min, 37° C., 200 rpm). Next the meshes were washed with water and reacted with DTT (15 mg/ml; 30 min, RT, mild shaking; 30 min at 4° C.). The meshes were quickly washed and reacted with Cy3/cleavable cross-linkers co-modified Ad-tPA, prepared as follows.

Three aliquots of 500 pl of the virus ($4.3 \times 10^{12}$/ml) were diluted each to 700 µl with 200 µl of carbonate-bicarbonate buffer (pH=9.3). Next, 150 µl of Cy3NHS (lmg/ml in the carbonate/bicarbonate buffer) and 75 µl of the cleavable cross-linker 2 (131A-55-3; 20 mg/ml of carbonate/bicarbonate buffer) were added to one of three virus aliquots (formulation 1).

The formulation 2 was prepared identically, however instead of rapidly hydrolysable cross-linker, a cross-linker with protracted hydrolysis kinetics, the cross-linker 2 was used at the same molar concentration (75 µl of 21.4 mg/ml solution in PBS).

Finally, the formulation 3 was prepared similarly to the formulation I, however, 25 µl instead of 75 µl of the cross-linker 2 were added. With all three Ad formulations, the conjugation was run for 30 min at 30° C. at 200 rpm, and for another 20 min at RT and no shaking. Conjugated Ad samples were purified via Sepharose B6 column primed with degassed PBS/3 mM EDTA. The fractions comprising 4 to 9 ml were collected (the purification yield of the procedure was ca 77, 86 and 75% for the formulations I, 2 and 3, respectively).

To obtain conversion factors between formulation fluorescence and particle numbers, the samples were assayed by fluorimetry against the Cy3 calibration curve immediately after spectrophotometry. The average extent of labeling was 2792, 2472 and 4152 Cy3 residues per virion for the formulations 1, 2 and 3, respectively.

The formulations 1 and 2 were diluted with 1 ml 0.36% Tween/PBS, to obtain 6 ml of 0.06% Tween/PBS-based formulations. The formulation 3 was diluted with 1 ml of 0.36% Tween/PBS and 1 ml of 0.06% Tween/PBS, to obtain 7 ml of 0.06% Tween/PBS-based formulation.

One ml aliquots of the formulation 1 ($2.695 \times 10^{11}$ particles) were added to the meshes 3-6. One ml aliquots of the formulation 2 ($3.01 \times 10^{11}$ particles) were added to meshes 7-10. One ml aliquots of the formulation #3 ($2.25 \times 10^{11}$ particles) were added to meshes 11-14 and to two control (PAA PB-treated) meshes 1 and 2. The conjugation (and mock conjugation) was carried out for 13 hours at 28° C. under shaking (200 rpm). The non-used residue of virus formulations (2 ml of suspensions 1 and 2, and 1 ml of the suspension 3) was exposed to the same conditions as the meshes under conjugation and served as non-depleted control. The supernatants of individual meshes were then assessed fluorimetrically and spectrophotometrically along with non-depleted control. Finally, the samples were examined by fluorescence microscopy, and 4 representative images of each mesh were taken. The specimens were placed into individual bottles, and 1 ml of 0.06% Tween/PBS were added. At the predetermined time points, the supernatants of the meshes and the mesh surfaces were assessed by fluorimetry and fluorescence microscopy, respectively.

Figure 6:
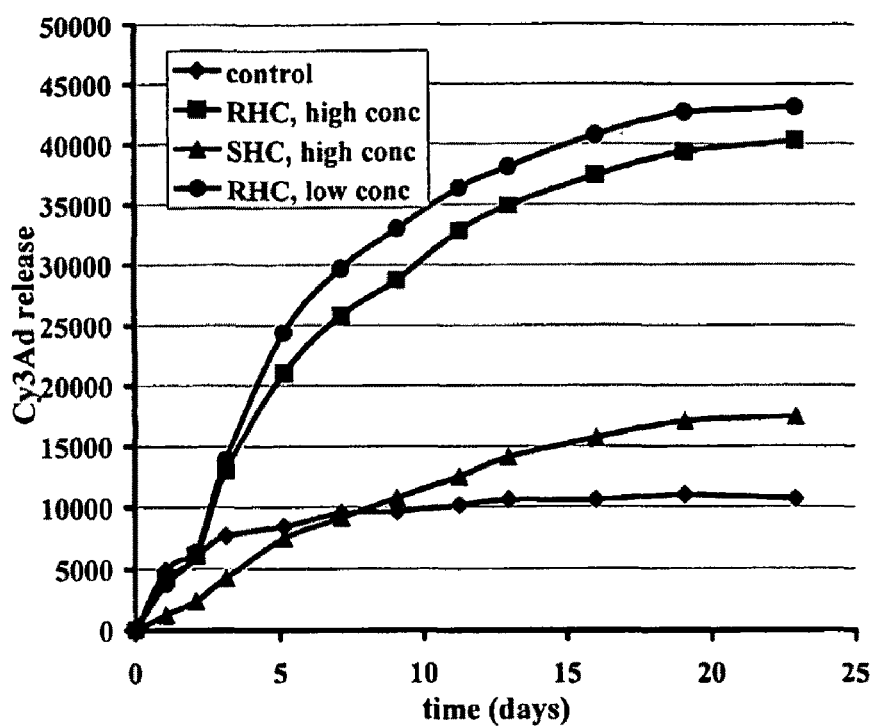
FIG. 6 is a graph depicting a release rate (by cumulative aliquots of Ad tethered via the slowly hydrolysable cross-linker 1 (SHC) and the rapidly hydrolysable cross-linker 2 (RHC). RHC is represented by two concentrations, FIG. 7 is a graph depicting Ad release tethered via the slowly hydrolysable cross-linker 1 (SHC) and the rapidly hydrolysable cross-linker 2 (RHC) by measuring the fluorescence intensity on the surface during the period of about 25 days.
Figure 7:
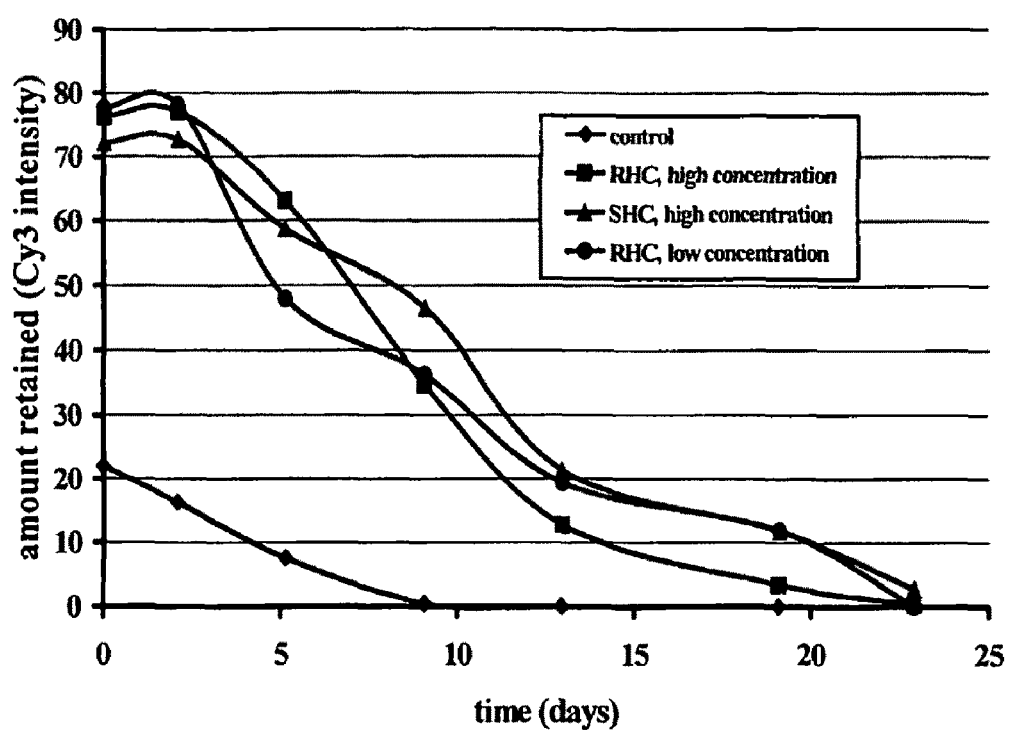

The release rate (by cumulative aliquots; FIG. 6) of Ad tethered via the slowly hydrolysable cross-linker 1 (SHC) was much flatter, than that for Ad attached via the rapidly hydrolysable cross-linker 2 (RHC). Additionally, lower concentration of RHC allows for faster release (steeper curve) than higher concentration of the same compound. The estimation of release by the fluorescence intensity on the surface (FIG. 7) parallels to some extent those data (especially on early time points). However, there is a concern that was not adequately addressed by the current experimental design. It appears that the illumination of the steel surface during microscopy caused a decay of Cy3, and partially compromised validity of the release results obtained by this method. However, since both experiments were conducted under the same conditions, this observation should not change the overall effect.

Example 7

In addition to the amplifier described in the Example 1, the following amplifier based on polyallylamine can be used in the amplification procedure. This amplifier is prepared as described below.

Polyallylamine hydrochloride (PAA HCl, Sigma-Aldrich, number average molecular weight $M_n \approx 10$ kDa, weight average molecular weight $M_w$, $\approx 15$ kDa, extent of polymerization $n \approx 100$) was transformed into the free PAA base by treatment in an aqueous solution with a strongly basic anionite Dowex G-55 (Sigma, OH-form). Water was then changed to 2-propanol, and a solution of PAA base in 2-propanol (containing ca. 1.1 mmol/g of $NH_2$ groups) was used for the further synthesis. This solution (2.207 g, 2.43 mmol of $NH_2$) was diluted with $CH_2Cl_2$ (5 ml), cooled in ice, and a solution of SPDP (Pierce, 0.379 g, 1.21 mmol) in $CH_2Cl_2$ was added dropwise in 2 min under stirring. The mixture was further stirred in ice for 20 min., and succinic anhydride (Sigma-Aldrich, 0.161 g, 1.61 mmol) was added in one portion. After stirring in ice for another 1 h, the mixture was vacuum-dried, and the residue of polymer was co-evaporated with ethyl acetate until solidification. The solid polymer was washed with ethyl acetate, dried and dissolved in water (10 ml) with addition of $KHCO_3$ (0.556 g, 5 55 mmol). The solution was filtered and acidified with $H_3PO_4$ to pH=3. The precipitate of polymer was filtered off, washed with water, ethyl acetate, and dried in vacuo. Yield 0.510 g. $^1H$ NMR ($D_2O+K_2CO_3$, pH=9) showed nearly equal modification with both 2-pyridyldithio and succinamoic groups $NHCOCH_2CH_2COOH$, with signals of the former appearing as 3 bands at δ 8.20, 7.48 and 7.02 ppm (1:2:1 in intensity) and $CH_2$ of the latter—at δ 2.41 ppm.

Example 8

Experiments were performed to test the effect of neutralizing antibodies on adenovirus attached to steel meshes by a hydrolyzable crosslinker (RHC, also referred to as HL2). Twelve meshes were pre-treated with isopropanol and nitric acid. The meshes were then reacted with 1.2% PrSSPAABP for 4 hours at 72° C. while shaking (200 rpm). The meshes were subsequently treated with TCEP (20 mg/ml in 0.1M acetic buffer) at 28° C. for 20 min while shaking. Meshes were washed with degassed water and reacted with PEI PDT at 28° C. overnight under argon atmosphere, and then stored at 4° C.

Ad-GFP (160 ul) was diluted with 500 ul CBB and reacted with either 10 ul of 10 mg/ml solution of cross-linker 2 in CBB for 55 min at 28° C., while shaking. This preparation (modified Ad-GFP) was filtered through Sepharose B6 into degassed PBS/EDTA and the eluted fraction was collected.

Meshes were treated with DTT (20 mg/ml), washed with degassed DDW, and reacted with modified Ad-GFP for 2 hours at 28° C., 200 rpm shaking, under argon.

Non-modified Ad-GFP (10 ul) ($5.36 \times 10^{12}$ particles/ml) was diluted with PBS to 500 ul and aliquoted into 160 ul aliquots. To each aliquot was added either 1.6 ul or 8 ul of AkAb (4 mg/ml stock) (neutralizing anti-knob antibody) or 8 ul of PBS. Washed meshes were placed into 160 ul of PBS with either no AkAb (control), 1.6 ul AkAb, or 8 ul of AkAb. Free and mesh-immobilized Ad was incubated with neutralizing Ab for 15 min at RT on a shaker. Aliquots (22 ul) of free Ad-GFP (either neutralized or non-neutralized) were added to subconfluent A10 cells (rat arterial smooth muscle cells) in a 96 well plate. Meshes bearing modified Ad-GFP were placed in parallel wells of cells on the same plate. To compensate for removal of the meshes from the neutralizing antibody when placing them on cells, two meshes were placed in wells containing AkAb in an amount equal to that transferred into the wells with the 22 ul aliquot of free Ad.

Figure 8:
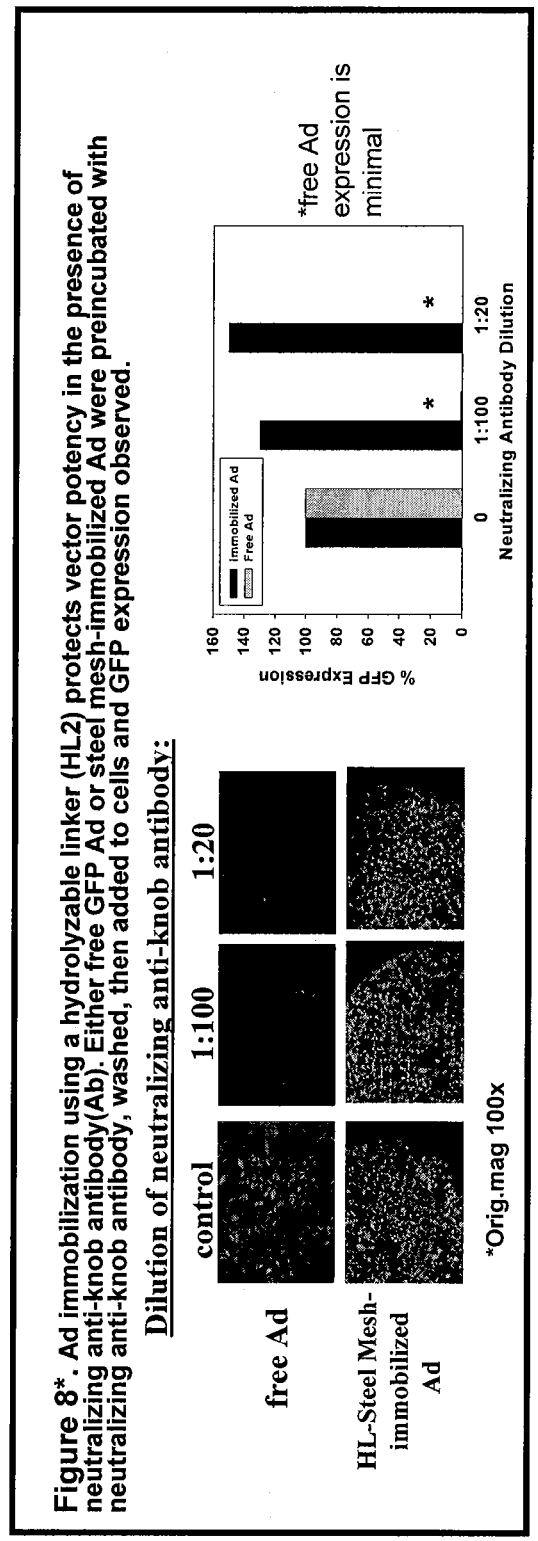
FIG. 8 contains fluorescence micrographs and a graph showing the effects of immobilization on antibody neutralization of adenovirus.

Viral transduction was assessed 24 h after addition of the free Ad or mesh-bound Ad by fluorescence microscopy and fluorometry. Results are shown in FIG. 8, which shows that immobilized (mesh-bound) adenovirus is protected from degradation initiated by neutralizing antibodies.

Example 9

Figure 9:
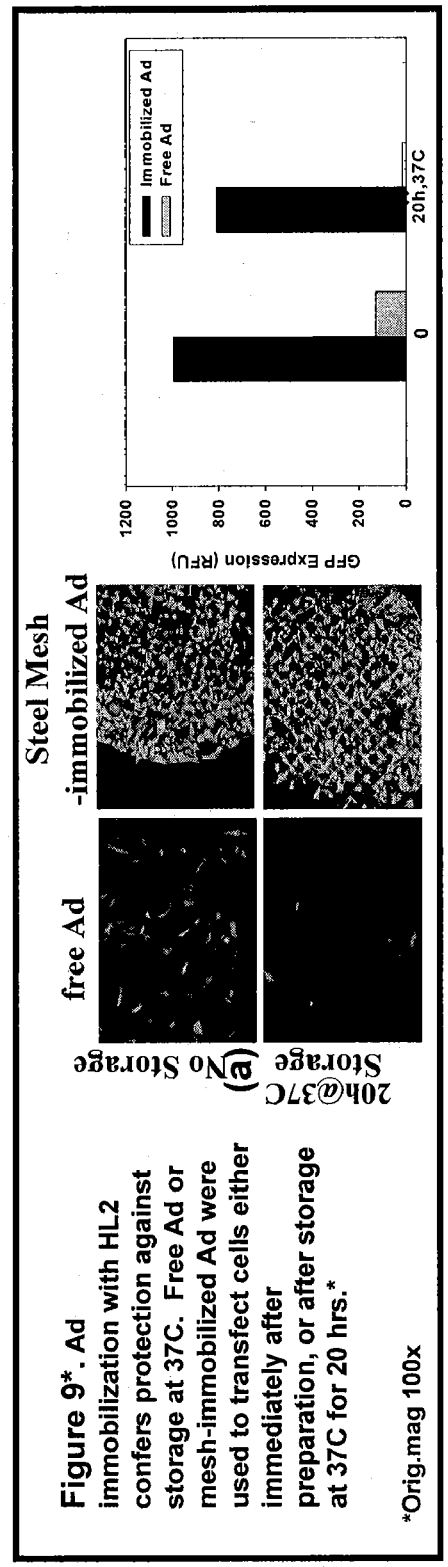
FIG. 9 contains fluorescence micrographs and a graph showing the effects of immobilization on heat and storage stability of adenovirus.

Meshes were prepared as described in Example 8. Free modified Ad-GFP ($3.75 \times 10^8$ particles) or mesh-bound modified Ad-GFP ($2 \times 10^8$ particles) were added to A10 cells for transfection either immediately after binding of modified Ad-GFP to the meshes, or after storage of the Ad-bound meshes at 37° C. for 20 hours. As shown in FIG. 9, immobilization of adenovirus on steel meshes through a hydrolyzable linker protects the virus from degradation during storage at elevated temperatures.

Example 10

Figure 10:
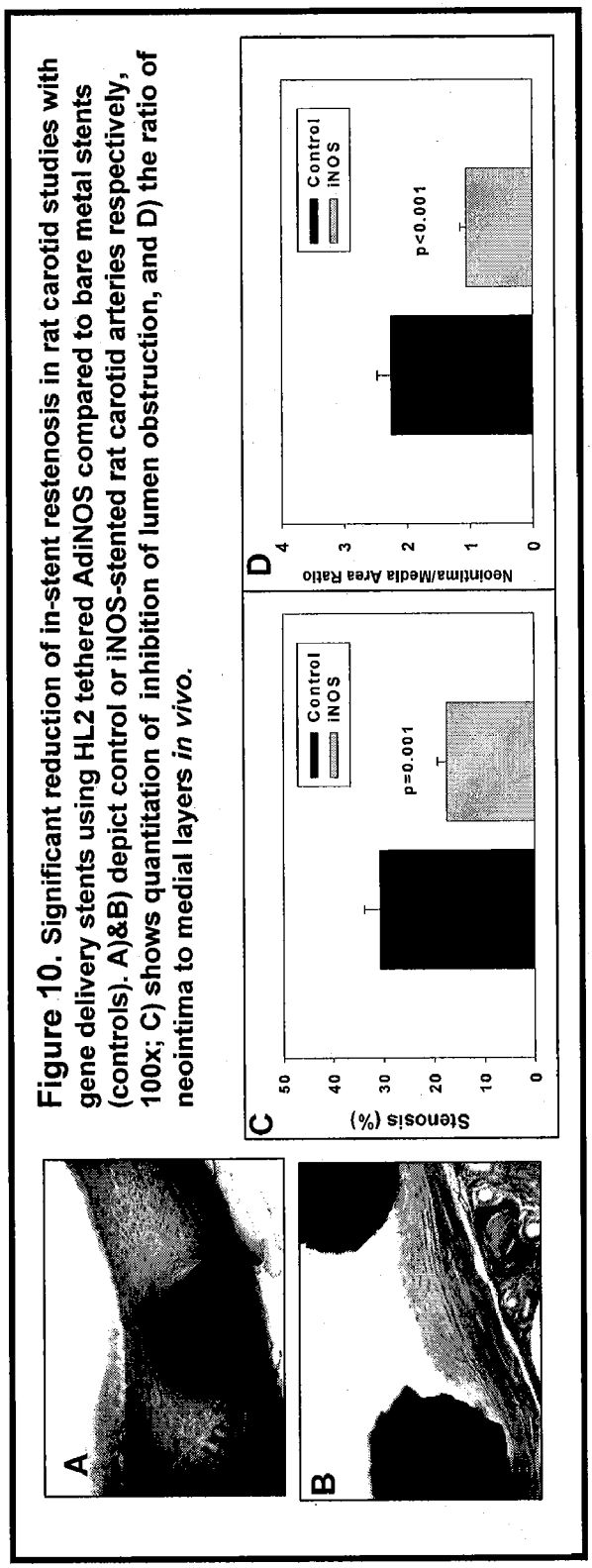
FIG. 10 contains light micrographs showing the effects of a gene delivery stent for inducible nitric oxide synthase (iNOS) vs. a bare metal stent on in-stent restenosis (A, B), and graphs quantifying the effects of a gene delivery stent for iNOS on stenosis (C) and on the ratio of neointimal to medial layers (D) in rat carotid arteries.

Stents were prepared and implanted as described in Example 5, except that stents were bound via a hydrolyzable cross-linker 2 with adenovirus encoding iNOS (Ad-iNOS) instead of Ad-GFP. Animals were sacrificed 14 days after implantation. The stented arteries were fixed in formalin for 48 hours and embedded in methyl methacrylate, sectioned at 70-80 um, and stained by the Verhoef-VanGiesen method. Sections were examined by light microscopy. Micrographs were captured as digital images under 50× magnification. Areas of lumen, neointima and media were calculated using Scion image-generated tracings of the respective arterial compartments. The extent of neointimal thickening was expressed as the ratio between the neointimal area and the area defined by the internal elastic lamina (% stenosis), and as the ratio between the neointimal and medial areas. FIG. 10 (A-D) shows that in-stent restenosis is significantly reduced in arteries bearing stents linked to Ad-iNOS via a hydrolyzable linker when compared with arteries bearing bare metal stents. A—tissue from artery with bare metal (control) stent; B—tissue from artery with Ad-iNOS-bearing stent; C—percent stenosis (lumen obstruction) for bare metal and Ad-iNOS stents; D—ratio of neointima to medial layers in stented arteries.

While the invention has been described in detail and with reference to specific examples thereof, it will be apparent to one skilled in the art that various changes and modifications can be made therein without departing from the spirit and scope thereof.

What is claimed is:

1. A composition for delivery of a biomaterial to an animal cell or a tissue, the composition comprising:
   (a) a biomaterial;
   (b) a biodegradable cross-linker portion having a hydrolyzable bond, wherein the biodegradable cross-linker portion is covalently bound to the biomaterial; and
   (c) a substrate, wherein the substrate is covalently bound to the biodegradable cross-linker portion, and wherein the hydrolyzable bond is positioned such that its hydrolysis results in release of the biomaterial from the substrate;
wherein the biomaterial comprises a virus vector, the biodegradable cross-linker portion is according to formula (b)

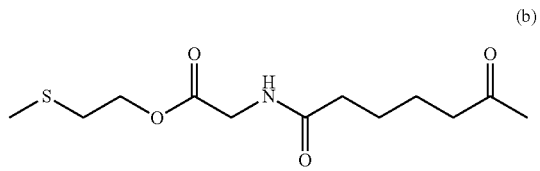

(b)

and the substrate comprises a metal.

* * * * *